United States Patent
Strano et al.

(10) Patent No.: US 9,980,668 B2
(45) Date of Patent: May 29, 2018

(54) PHOTOLUMINESCENT NANOSTRUCTURE-BASED SENSORS

(75) Inventors: Michael S. Strano, Lexington, MA (US); Paul W. Barone, Jamaica Plain, MA (US); Jin-Ho Ahn, Cambridge, MA (US); Kyungsuk Yum, Cambridge, MA (US); Thomas P. McNicholas, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days. days.

(21) Appl. No.: 13/562,403

(22) Filed: Jul. 31, 2012

(65) Prior Publication Data

US 2013/0035567 A1    Feb. 7, 2013

Related U.S. Application Data

(60) Provisional application No. 61/513,790, filed on Aug. 1, 2011.

(51) Int. Cl.
*A61B 5/1455* (2006.01)
*A61B 5/1459* (2006.01)
(Continued)

(52) U.S. Cl.
CPC ........ *A61B 5/1459* (2013.01); *A61B 5/14532* (2013.01); *G01N 33/542* (2013.01);
(Continued)

(58) Field of Classification Search
USPC .................................. 600/310–344
See application file for complete search history.

(56) References Cited

U.S. PATENT DOCUMENTS

| | | | | |
|---|---|---|---|---|
| 5,629,168 A | * | 5/1997 | Kricka | ........................... 435/28 |
| 2001/0034500 A1 | * | 10/2001 | March | ........................... 604/66 |

(Continued)

FOREIGN PATENT DOCUMENTS

| WO | WO 2010/099446 | 9/2010 |
|---|---|---|
| WO | WO 2012/030961 | 3/2012 |

OTHER PUBLICATIONS

International Search Report and Written Opinion of the International Searching Authority dated Nov. 14, 2012 for PCT/US2012/048841.

(Continued)

*Primary Examiner* — Eric Winakur
*Assistant Examiner* — Marjan Fardanesh
(74) *Attorney, Agent, or Firm* — Steptoe Johnson LLP

(57) ABSTRACT

A composition for sensing an analyte can include a photoluminescent nanostructure complexed to a sensing polymer, where the sensing polymer includes an organic polymer non-covalently bound to the photoluminescent nanostructure and an analyte-binding protein covalently bound to the organic polymer, and where the analyte-binding protein is capable of selectively binding the analyte, and the analyte-binding protein undergoes a substantial conformational change when binding the analyte. Separately, a composition for sensing an analyte, can include a complex, where the complex includes a photoluminescent nanostructure in an aqueous surfactant dispersion and a boronic acid capable of selectively reacting with an analyte. The compositions can be used in devices and methods for sensing an analyte.

21 Claims, 16 Drawing Sheets

(51) Int. Cl.
*A61B 5/145* (2006.01)
*G01N 33/542* (2006.01)
*G01N 33/543* (2006.01)
*G01N 33/58* (2006.01)
*G01N 33/66* (2006.01)

(52) U.S. Cl.
CPC ..... *G01N 33/54373* (2013.01); *G01N 33/582* (2013.01); *G01N 33/587* (2013.01); *G01N 33/66* (2013.01)

(56) References Cited

U.S. PATENT DOCUMENTS

2003/0027240 A1* 2/2003 Asher et al. ............. 435/25
2007/0292896 A1* 12/2007 Strano et al. ........... 435/7.9
2010/0279421 A1* 11/2010 Strano et al. ........... 436/86

OTHER PUBLICATIONS

Barone, Paul et al., "Single walled carbon nanotubes as reporters for the optical detection of glucose," Journal of Diabetes Science and Technology, Diabetes Technology Society, vol. 3, No. 2, Jan. 1, 2009, pp. 242-252.

Barone, P W et al., "Near-infrared optical sensors based on single-walled carbon nanotubes," Nature Materials Nature Publishing Group, vol. 4, No. 1, Jan. 2005, pp. 86-92.

* cited by examiner

PHOTOLUMINESCENT NANOSTRUCTURE-BASED SENSORS

CLAIM OF PRIORITY

This application claims priority to provisional U.S. application No. 61/513,790, filed Aug. 1, 2011, which is incorporated by reference in its entirety.

FEDERALLY SPONSORED RESEARCH OR DEVELOPMENT

This invention was made with government support under Grant No. NSF0753036 awarded by the National Science Foundation. The government has certain rights in the invention.

STATEMENT REGARDING FEDERALLY SPONSORED RESEARCH OR DEVELOPMENT

This invention was made with government support under Grant No. CBET 0753036, awarded by the National Institutes of Health. The government has certain rights in this invention.

TECHNICAL FIELD

The present invention generally relates to sensors based on photoluminescent nanostructures.

BACKGROUND

In vivo sensors are of particular interest in the biomedical field, where continuous and/or real time patient data can be desirable; in particular, sensors that can detect and measure the levels of biological compounds (e.g., metabolites). Such sensors can involve a sensor material that interacts with an analyte, where the interaction results in changes in how the sensor material interacts with light, e.g., changes in the absorption or luminescence properties of the sensor material. Several photonics applications have been proposed for in vivo sensing such as, for example, surface enhanced Raman spectroscopy (SERS). However, many proposed methods are expensive, require high resolution, and involve the use of bulky equipment.

Diabetes affects nearly 17.9 million people in the United States alone, with 1.6 million new cases being diagnosed each year. Diabetes was the seventh leading cause of death in the United States as of 2006, and is still rising. Current treatments involve monitoring of glucose levels in a patient's body. This monitoring allows the patient to appropriately treat glucose levels which are outside of the safe range, and thus avoid complications which could otherwise result.

The basic glucose monitoring device in use today, a finger-stick glucose monitor, has certain disadvantages. These include the pain associated with the finger stick, and the discontinuous nature of the information provided. With such devices, a patient must rely on a few single-point measurements taken throughout the day to monitor his or her blood glucose levels. Accordingly, there remains a need for a real-time, continuous blood glucose monitor.

SUMMARY

Sensors based on photoluminescent nanostructures, and methods of making and using them, are described. Photoluminescent nanostructures (e.g., single-walled carbon nanotubes, or SWNTs) can be combined with an analyte-binding group in such a way that the photoluminescence is altered when the analyte interacts with the analyte binding group. For example, when the analyte in question is glucose, the analyte binding group can be a glucose binding protein or a boronic acid. The photoluminescent nanostructures can be packaged in a biocompatible matrix suitable for use in vivo to produce a real-time, continuous and long-term glucose monitor.

In one aspect, a composition for sensing an analyte includes a photoluminescent nanostructure complexed to a sensing polymer, where the sensing polymer includes an organic polymer non-covalently bound to the photoluminescent nanostructure and an analyte-binding protein covalently bound to the organic polymer, where the analyte-binding protein is capable of selectively binding the analyte, and the analyte-binding protein undergoes a substantial conformational change when binding the analyte.

In a related aspect, a device for sensing an analyte includes a semi-permeable membrane enclosing a composition, where the composition includes a photoluminescent nanostructure complexed to a sensing polymer, where the sensing polymer includes an organic polymer non-covalently bound to the photoluminescent nanostructure and an analyte-binding protein covalently bound to the organic polymer, where the analyte-binding protein is capable of selectively binding the analyte, and the analyte-binding protein undergoes a substantial conformational change when binding the analyte.

In a related aspect, a method for sensing an analyte includes providing a composition, where the composition includes a photoluminescent nanostructure complexed to a sensing polymer, where the sensing polymer includes an organic polymer non-covalently bound to the photoluminescent nanostructure and an analyte-binding protein covalently bound to the organic polymer, where the analyte-binding protein is capable of selectively binding the analyte, and the analyte-binding protein undergoes a substantial conformational change when binding the analyte, and contacting the composition with a sample suspected of containing the analyte.

The photoluminescent nanostructure can be a carbon nanotube. The carbon nanotube can be a SWNT. The analyte-binding protein can be a periplasmic binding protein. The analyte-binding protein can be a glucose binding protein, and the analyte can be glucose. The organic polymer can be a carboxylated PVA.

In another aspect, a composition for sensing an analyte includes a complex, where the complex includes a photoluminescent nanostructure in an aqueous dispersion and a boronic acid capable of selectively reacting with an analyte.

In a related aspect, a device for sensing an analyte includes a hydrogel particle encapsulating a composition, where the composition includes a complex, where the complex includes a photoluminescent nanostructure in an aqueous dispersion and a boronic acid capable of selectively reacting with an analyte.

In a related aspect, a method for sensing an analyte includes providing a composition, wherein the composition includes a complex, where the complex includes a photoluminescent nanostructure in an aqueous dispersion and a boronic acid capable of selectively reacting with an analyte, and contacting the composition with a sample suspected of containing the analyte.

The photoluminescent nanostructure can be a carbon nanotube. The carbon nanotube can be a SWNT. The composition can further include the analyte. The analyte can be a monosaccharide; the monosaccharide can be glucose.

The boronic acid can be selected from the group consisting of: 3-aminophenylboronic acid, 4-chlorophenylboronic acid, 4-carboxyphenylboronic acid, naphthalene-1-boronic acid, 3-nitrophenylboronic acid, benzene-1,4-diboronic acid, 2-naphthylboronic acid, 1-thianthrenylboronic acid, 4-cyanophenylboronic acid, 4-methyl-1-naphthaleneboronic acid, 6-methoxy-2-naphthaleneboronic acid, 6-ethoxy-2-naphthaleneboronic acid, 3-biphenylboronic acid, 8-quinolinylboronic acid, pyrene-1-boronic acid, 9,9-dihexylfluorene-2,7-diboronic acid, acenaphthene-5-boronic acid, 10-bromoanthracene-9-boronic acid, 4-(diphenylamino)phenylboronic acid, 4-(4'-methoxybenzyloxy)phenylboronic acid, 444'42-pentyloxy)phenyl)phenylboronic acid, 2-(tert-butyldimethylsilyloxy)naphthalene-6-boronic acid, 9-anthraceneboronic acid, 5-bromopyridine-3-boronic acid, 9-phenanthracenylboronic acid, 4-bromo-1-naphthaleneboronic acid, 2-aminopyrimidine-5-boronic acid, indazole-4-boronic acid, fluorene-2-boronic acid, and indazole-6-boronic acid.

Other aspects, embodiments, and features will become apparent from the following description, the drawings, and the claims.

DETAILED DESCRIPTION

Figure 1:
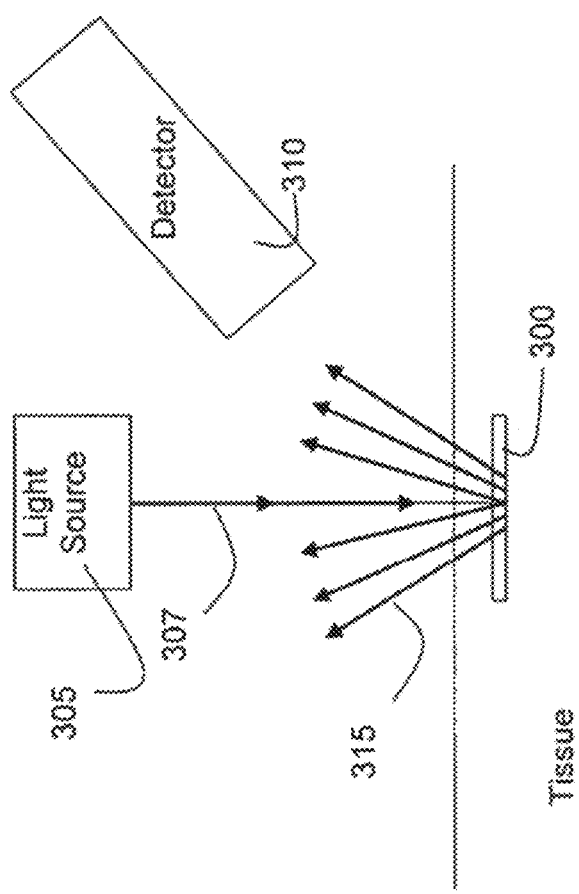
FIG. 1 is a schematic depiction of a sensor implanted in tissue.

Compositions including photoluminescent nanostructures are described. Methods and systems involving the compositions are also described. Related compositions, methods, and systems are described in, e.g., U.S. Patent Application Publication Nos. 2007/0292896 and 2010/0279421, and in U.S. patent application Ser. No. 13/090,199 filed 19 Apr. 2011, each of which is incorporated by reference in its entirety.

In general, an analyte sensing composition can include photoluminescent nanostructure in a complex (e.g., a non-covalent complex) with a polymer, such as a sensing polymer. The photoluminescent nanostructure can be a carbon nanotube. A sensing polymer can include, for example, an organic polymer (including but not limited to poly(alkylene glycols) (e.g., poly(ethylene glycol)), poly(vinyl alcohol), carboxylated poly(vinyl alcohol), poly(vinyl chloride), polysorbitan esters (e.g., polyoxyethylene sorbitan fatty acid esters), and copolymers of these, whether with each other or with other polymers), a protein, a polypeptide, or a polysaccharide.

In the sensing composition, the sensing polymer can complexed with the carbon nanotube to provide individually dispersed carbon nanotubes with no electronic interaction or minimal electronic interaction with other carbon nanotubes in the composition. The sensing polymer can selectively interact with an analyte. The term "selective" indicates an interaction that can be used to distinguish the analyte in practice from other chemical species, even species which may be structurally related or similar to the analyte, in the system in which the sensor and sensing composition is to be employed. The interaction can be, for example, a reversible or irreversible non-covalent binding interaction; a reversible or irreversible covalent binding interaction (i.e., a reaction wherein a covalent bond between the sensing polymer and the analyte is formed); or catalysis (e.g., where the sensing polymer is an enzyme and the analyte is a substrate for the enzyme).

The term "selective binding" is thus used to refer to an interaction, typically a reversible non-covalent binding interaction, between a sensing polymer and an analyte, which is substantially stronger than the interaction between the sensing polymer and species that are related in chemical structure to the analyte. The strength of a selective binding interaction may be determined with reference to, for example, an equilibrium binding constant for a given set of conditions.

Enzymes, antibodies (and antibody fragments) and receptors, among other proteins, can exhibit specific binding which may in some cases be selective. Other polymers, such as polysaccharides may function as ligands (e.g., for binding to a protein) or as a member of a binding pair. Selective binding can provide the selectivity needed to detect a selected analyte (or relatively small group of related analytes) in a complex mixture, e.g., in a biological fluid or tissue. For example, selective binding of a substrate to an enzyme can provide the desired level of selectivity needed to detect a selected analyte (which is the enzyme substrate). Sensing polymers can be chosen to provide selective interactions with one or more analytes. Preferably a particular sensing polymer can have a selective interaction with just one analyte; in other words, the selectivity is such that the sensing polymer can distinguish between the analyte and virtually all other chemical species.

The term "analyte" refers to any chemical species, suspected of being present in a sample, which the presence or absence of in the sample is to be determined, or the quantity or concentration of in the sample is to be determined. Analytes can include small molecules, such as sugars, steroids, antigens, metabolites, drugs, and toxins; and polymeric species such as proteins (e.g., enzymes, antibodies, antigens). In specific embodiments, analytes are one member of a binding partner pair. In some embodiments, analytes are monosaccharides, e.g., glucose. The compositions, methods, and systems described can be particularly well suited to the detection and/or quantitation of analytes in solutions, such as biological fluids. The compositions, methods, and systems described can also be particularly well suited to the detection and/or quantitation of analytes in biological tissues, including tissues in vivo.

The sensing polymer can be formed by derivatization of a polymer with one or more chemically selective species which provide for selective or specific interaction with one or more analytes. Polymers that may be derivatized to form sensing polymers include, but are not limited to, poly (alkylene glycols) such as poly(ethylene glycol), poly(vinyl alcohol), poly(vinyl chloride), polysorbitan esters (e.g., polyoxyethylene sorbitan fatty acid esters), and copolymers of these, whether with each other or with other polymers. Each sensing polymer may be derivatized to carry one or more chemically selective species or moieties which are each selective for the same analyte. A sensing polymer may be derivatized to carry one or more chemically selective species or moieties which are each selective for a different analyte. Thus a single composition may be responsive to a single analyte, or to more than one different analytes. In specific embodiments, a sensing polymer contains covalently bound, chemically selective species or moieties selective for a single analyte of interest. The use of polymers which carry one such selective chemical species or moiety may be beneficial to prevent aggregation of the complexes of the photoluminescent nanostructure and the sensing polymer. Such aggregation can be detrimental in analyte sensing applications. The chemically selective species or moiety may be directly bonded to the polymer or indirectly bonded through a linker group.

The sensing polymer can be a sensing protein or a sensing polysaccharide. The sensing protein may be a naturally-occurring protein or recombinant protein that exhibits a selective interaction with an analyte. The sensing protein can interact directly with an analyte (e.g., by binding or reaction) or can interact indirectly with the analyte by interaction (e.g., by binding or reaction) with another chemical species which in turn interacts with the analyte. The sensing protein may be formed by chemical derivatization of a protein that does not exhibit any selective interaction with an analyte. For example, the sensing protein may be formed from a protein that is derivatized covalently to carry one or more chemically selective species (or moieties) which individually or collectively provide for selective interaction with one or more analytes. Proteins may be derivatized at one or more termini or at one or more amino acid side changes (e.g., those of lysine, glutamine, arginine, serine, aspartate, glutamate, etc.) to provide for chemical selectivity.

For some proteins, binding of the analyte causes a substantial conformational change in the protein. A substantial conformational change is one that causes a relatively large movement of one or more substructures of the protein. For example, a substantial conformational change can involve a relative movement of domains of the protein, or a relative movement of subunits of a multimeric protein. In some cases, the protein can be considered to have distinct conformations, depending on whether or not the analyte is bound. For example, some proteins can be described as being in an "open" or "closed" state depending on whether or not the analyte is bound; "open" and "closed" can describe the relative size of a cleft between two domains (i.e., the cleft is larger or more "open" in one state and smaller or more "closed" in another state).

Without intending to be bound by a particular theory, in the context of a sensor, the substantial conformational change can affect the photoluminescence properties (e.g., intensity or peak wavelength) of a photoluminescent nanostructure. The substantial conformational change can provide a mechanical force or actuation on the photoluminescent nanostructure; in other words, the substantial conformational change alters how the sensing protein interacts with or impinges on the photoluminescent nanostructure, which in turn affects the photoluminescence properties.

A sensing polysaccharide can provide for selective interaction with an analyte. The sensing polysaccharide may be naturally occurring, for example isolated from nature, chemically derivatized, chemically modified, or chemically synthesized. The sensing polysaccharide can interact directly with an analyte (e.g., by binding or reaction) or can interact indirectly with the analyte by interaction (e.g., by binding or reaction) with another chemical species which in turn interacts with the analyte. The specific structure of the polysaccharide or the presence of a specific monosaccharide may facilitate a selective interaction with an analyte. The sensing polysaccharide may be formed by chemical derivatization or modification of a polysaccharide that does not exhibit any selective interaction with an analyte. For example, the sensing polysaccharide may be formed from a polysaccharide that is derivatized covalently to carry one or more chemically selective species (or moieties) which individually or collectively provide for selective interaction with one or more analytes. Polysaccharides may be derivatized at any available location of the polymer that is reactive to provide for chemical selectivity. Polysaccharides that are useful, for example, as sensing polymers include those polysaccharides which bind to a binding partner, for example a protein, that also binds to a monosaccharide analyte. Polysaccharides include those having 10 or more monosaccharide units, 20 or more monosaccharide units, 10 or more disaccharide units, or 20 or more disaccharide units.

As used herein, the term "nanostructure" refers to articles having at least one cross-sectional dimension of less than about 1 µm, less than about 500 nm, less than about 250 nm, less than about 100 nm, less than about 75 nm, less than about 50 nm, less than about 25 nm, less than about 10 nm, or, in some cases, less than about 1 nm. Examples of nanostructures include nanotubes (e.g., carbon nanotubes), nanowires (e.g., carbon nanowires), graphene, and quantum dots, among others. In some embodiments, the nanostructures include a fused network of atomic rings.

A "photoluminescent nanostructure," as used herein, refers to a class of nanostructures that are capable of exhibiting photoluminescence. Examples of photoluminescent nanostructures include, but are not limited to, carbon nanotubes (e.g., single-walled and double-walled carbon nanotubes), semiconductor quantum dots, semiconductor nanowires, and graphene, among others. In some embodiments, photoluminescent nanostructures exhibit fluorescence. In some instances, photoluminescent nanostructures exhibit phosphorescence.

Carbon nanotubes are carbon nanostructures in the form of tubes, generally ranging in diameter from about 0.5-200 nm, (more typically for single-walled carbon nanotubes from about 0.5-5 nm) The aspect ratio of nanotube length to nanotube diameter is greater than 5, ranges from 10-2000 and more typically 10-100. Carbon nanotubes may be single-walled nanotubes (a single tube) or multi-walled comprising with one or more smaller diameter tubes within larger diameter tubes. Carbon nanotubes are available from various sources, including commercial sources, or synthesis employing, among others, arc discharge, laser vaporization, the high pressure carbon monoxide processes.

The following references provide exemplary methods for synthesis of carbon nanotubes: U.S. Pat. No. 6,183,714; WO/2000/026138; WO/2000/017102; A. Thess et al. Science (1996) 273:483; C. Journet et al. Nature (1997) 388, 756; P. Nikolaev et al. Chem. Phys. Lett. (1999) 313:91; J. Kong et al. Chem. Phys. Lett. (1998) 292: 567; J. Kong et al. Nature (1998) 395:878; A. Cassell et al. J. Phys. Chem. (1999) 103:6484; H. Dai et al. J. Phys. Chem. (1999) 103:11246; Bronikowski, M. J., et al., Gas-phase production of carbon single-walled nanotubes from carbon monoxide via the HiPco process: a parametric study. J. Vac. Sci. Tech. A, 2001. 19(4): p. 1800-1804; Y. Li et al. (2001) Chem. Mater. 13:1008; N. Franklin and H. Dai (2000) Adv. Mater. (2000) 12:890; A. Cassell et al. J. Am. Chem. Soc. (1999) 121:7975; and International Patent Applications WO 00/26138, WO 03/084869, and WO 02/16257; each of which is incorporated by reference in its entirety. Carbon nanotubes produced in such methods are typically polydisperse samples containing metallic and semi-conducting types, with characteristic distributions of diameters.

A method for separating single-walled carbon nanotubes by diameter and conformation based on electronic and optical properties has been reported (WO 03/084869, which is incorporated by reference in its entirety. The method can be employed to prepare carbon nanotube preparations having enhanced amounts of certain single walled carbon nanotube types. Narrow (n, m)-distributions of single-walled carbon nanotubes are reported using a silica-supported Co—Mo catalyst. M. Meng et al. Science (2003) 302 (November) 1545 (which is incorporated by reference in its entirety) report nanotube separation by anion exchange chromatography of carbon nanotubes wrapped with single-stranded DNA. Early fractions are reported to be enriched in smaller diameter and metallic nanotubes, while later fractions are enriched in larger diameter and semi-conducting nanotubes.

Carbon nanotube compositions generally useful in sensors can exhibit optical properties which are sensitive to the environment of the nanotube, i.e., optical properties which can be modulated by changes in the environment of the nanotube. More specifically, carbon nanotube compositions useful in sensors can be SWNTs, particularly semiconducting SWNTs, which can exhibit luminescence, and more specifically which exhibit photo-induced band gap fluorescence. Carbon nanotube compositions which exhibit luminescence include SWNTs which when electronically isolated from other carbon nanotubes exhibit luminescence, including fluorescence and particularly those which exhibit fluorescence in the near-IR. Carbon nanotube compositions can include individually dispersed semiconducting SWNTs exhibiting luminescence, particularly photo-induced band gap fluorescence. Carbon nanotube compositions may also include MWNT and other carbon nanomaterials as well as amorphous carbon. Preferably carbon nanotube compositions can include a substantial amount of semiconducting SWNTs, e.g., 25% or more, or 50% or more by weight of such SWNTs. In general, carbon nanotube compositions will contain a mixture of semiconducting SWNTs of different sizes which exhibit fluorescence at different wavelengths.

Single walled carbon nanotubes are sheets of graphene—single layer of graphite—rolled into a molecular cylinder and indexed by a vector connecting two points on the hexagonal lattice that conceptually forms the tubule with a given "chiral" twist. Hence, (n,m) nanotubes are those formed by connecting the hexagon with one n units across and m units down (n>m by convention). Carbon nanotubes show a relationship between geometric and electronic structure: the 1-D nature of the nanotube exerts a unique quantization the circumferential wave-vector and hence, simple perturbations of this chirality vector yield substantial changes in molecular properties. When $|n-m|=0$, the system is metallic in nature while if $|n-m|=3q$ (with being q a nonzero integer) the nanotube possesses a small curvature induced gap and if $|n-m|\neq3q$ then the system is semiconducting with a measurable band-gap.

The sensing composition optionally contains SWNTs that are not semiconducting, i.e. metallic SWNTs, that are complexed with one or more proteins or other polymers, SWNTs (semiconducting or metallic) that are fully or partially complexed with proteins and/or polymers and/or surfactants, other carbon nanotubes or other carbon nanostructured materials that are complexed with protein (which may or may not be sensing proteins), polymers (which may or may not be sensing polymer) and/or surfactant, as well as aggregates, including ropes, of SWNTs, or aggregates of other carbon nanotubes or nanostructured materials. The sensing composition may further contain amorphous carbon and other byproducts of carbon nanotube synthesis, such as residual catalyst. Preferably, the types and levels of any of these optional components are sufficiently low to minimize detrimental effects on the function of the sensing composition.

Carbon nanotube/polymer complexes can be made by initial formation of individually dispersed carbon nanotubes. Individually dispersed nanotubes can be formed essentially as previously described by dispersion of carbon nanotube product in aqueous surfactant solution employing high-sheer mixing and sonication to disperse the nanotubes in surfactant, followed by centrifugation to aggregate bundles or ropes of nanotubes and decanting of the upper portion (e.g., 75-80%) of the supernatant to obtain micelle-suspended carbon nanotube solutions or dispersions (e.g., containing 20-25 mg/L of carbon nanotubes). Surfactant-dispersed carbon nanotubes are contacted with polymer solutions, preferably aqueous solutions of polymer, and subjected to dialysis under conditions in which the surfactant is removed without removal of the polymer or carbon nanotube. As surfactant is removed by dialysis, carbon nanotube/polymer complexes are formed.

The amount and type of surfactant employed for dispersion of carbon nanotubes can be readily determined employing methods that are well-known in the art. As noted in detail below, the surfactant employed must be compatible with the components of the sensing compositions, particularly with the sensing polymer, specifically with the sensing protein. The surfactant must not destroy the function of the sensing polymer or sensing protein. In certain cases, the surfactant must be a non-denaturing surfactant that does not significantly detrimentally affect the function (e.g., binding or enzymatic function) of the protein or other polymer. The amount of surfactant needed to disperse the carbon nanotubes can be determined by routine experimentation. It is preferred to employ the minimum amount of surfactant needed to provide individually dispersed carbon nanotubes. Surfactants are typically employed between about 0.1% to about 10% by weight. (more typically from 0.5% to 5% by weight) in aqueous solution to disperse carbon nanotubes.

For the formation of carbon nanotube/protein complexes, the surfactant originally employed to form the individually dispersed carbon nanotubes is replaced with a non-denaturing surfactant. For example, 1% by weight in water of sodium dodecylsulfate (SDS) can be replaced by 2% by weight in water of sodium cholate. Surfactant-dispersed carbon nanotubes are contacted in aqueous solution with functional protein or other polymer and subjected to dialysis under conditions in which the surfactant is removed without removal of the protein or carbon nanotube and the protein retains function. As surfactant is removed by dialysis, carbon nanotube/protein complexes are formed. The surfactant employed is of sufficiently low molecular weight to be removed by dialysis while the polymer is not.

Complexes of carbon nanotubes with sensing polymers can be prepared by methods other than the dialysis method specifically described herein. In some cases, the polymer may be complexed with the nanotube simply by contacting the nanotube with a sufficient amount of polymer and applying vigorous mixing (e.g., sonication), if necessary to obtain dispersed nanotubes. In other cases, an already dispersed nanotube composition comprising surfactant or polymer which functions for dispersion of the nanotube may be contacted with a sufficient amount of the sensing polymer and if necessary apply vigorous mixing to displace at least a portion of the surfactant or polymer already associated with the nanotube.

The preparation of surfactant dispersed carbon nanotubes employs vigorous mixing, for example high shear mixing, which may be provided using a high speed mixer, a homogenizer, a microfluidizer or other analogous mixing methods known in the art. Sonication, including various ultrasonication methods can be employed for dispersion. Preferred methods for dispersion involve a combination of high sheer mixing and sonication. See, for example, WO 03/050332 and WO 02/095099, each of which is incorporated by reference in its entirety.

In some embodiments, analyte sensing compositions include one or more carbon nanotube/protein complexes. In these complexes, one or more protein molecules are non-covalently associated with the carbon nanotube. Preferably, the protein molecule or molecules complexed with the carbon nanotube provide monolayer coverage or less of the carbon nanotube by protein. The complexed protein retains its biological function and the complexed carbon nanotube is a semi-conducting carbon nanotube which exhibits band gap fluorescence.

In some embodiments, analyte sensing compositions include one or more carbon nanotube/polysaccharide complexes. In these complexes, one or more polysaccharide molecules are non-covalently associated with the carbon nanotube. Preferably, the polysaccharide molecule or molecules complexed with the carbon nanotube provide monolayer coverage or less of the carbon nanotube by protein. The complexed polysaccharide retains its biological function and the complexed carbon nanotube is a semi-conducting carbon nanotube which exhibits band gap fluorescence.

Non-denaturing surfactants include anionic surfactants, non-ionic surfactants and zwitterionic (or amphoteric) surfactants. The term denature (or denaturing) is used herein with respect to protein structure and function. A denatured protein is one that has lost its functional structure. Contact with surfactants, as well as other environmental changes (e.g., temperature or pH changes), can cause structural changes in proteins, and these structural changes can affect one or more of the biological functions of the protein. For example, a denatured enzyme will no longer exhibit enzymatic function. Contact with a non-denaturing surfactant does not have any significant detrimental effect on one or more of the biological functions of a given protein. A normally denaturing surfactant may function as a non-denaturing surfactant over a selected concentration range or with respect to certain proteins which are more resistant to its denaturing effect than most other proteins.

Non-denaturing surfactants include, among others, bile acids and derivatives of bile acids, e.g., cholate (salts of cholic acid, particularly sodium cholate), deoxycholate (salts of deoxycholic acid, particularly sodium deoxycholate), sulfobetaine derivatives of cholic acid, particularly 3-[(3-cholamidopropyl)-dimethylammonio]-1-propanesulfonate (CHAPS); carbohydrate-based surfactants, for example, alkyl glucosides, particularly n-alkyl-β-glucosides (more specifically, n-octyl-α-glucoside (OG)), alkyl thioglucosides, particularly n-alkyl-β-thioglucosides (more specifically, n-octyl-β-thioglucoside (OTG)); alkyl maltosides, particularly n-alkyl-β-maltosides (more specifically, n-dodecyl-β-glucoside); alkyl dimethyl amine oxides (e.g., ($C_6$-$C_{14}$) alkyldimethyl amine oxides, particularly lauryidimethyl amine oxide), non-ionic polyoxyethylene surfactants, e.g., Triton™ X-100 (or octyl phenol ethoxylate), Lubrol™ PX, Chemal LA-9 (polyoxyethylene(9)lauryl alcohol); and glycidols, e.g., p-sonomylphenoxypoly(glycidol) (Surfactant 10G). A normally non-denaturing surfactant may function as a denaturing surfactant over a selected concentration range or with respect to certain proteins which are more sensitive to its denaturing effect than most other proteins.

Non-denaturing surfactant can also include mixtures of non-denaturing surfactants with denaturing surfactant where the amount of denaturing surfactant is sufficiently low in the mixture to avoid detrimental effect on the protein. Denaturing of a protein by a given surfactant is dependent upon the concentration of surfactant in contact with the protein and may also depend upon other environmental conditions (temperature, pH, ionic strength, etc.) to which the protein is being subjected. The denaturing effects of a selected surfactant, at selected concentrations, upon a selected protein can be readily assessed by methods that are well-known in the art.

Surfactants preferred for use in the preparation of carbon nanotube complexes are dialyzable, i.e., capable of being selectively removed form a surfactant dispersed carbon nanotubes by dialysis without significant removal of carbon nanotubes or the polymers that are to be complexed with the carbon nanotubes. Dialyzable, non-denaturing surfactants include, among others, bile acids and derivatives of bile acids, e.g., cholate (salts of cholic acid, particularly sodium cholate), deoxycholate (salts of deoxycholic acid, particularly sodium deoxycholate), sulfobetaine derivatives of cholic acid, particularly 3-[(3-cholamidopropyl)-dimethylammonio]-1-propanesulfonate (CHAPS); carbohydrate-based surfactants, for example, alkyl glucosides, (e.g., $C_6$-$C_{14}$ alkyl glucosides), particularly n-alkyl-β-glucosides (more specifically, n-octyl-β-glucoside (OG)), alkyl thioglucosides, (e.g., $C_6$-$C_{14}$ alkyl thioglucosides), particularly n-alkyl-β-thioglucosides (more specifically, n-octyl-β-thioglucoside (OTG)); alkyl maltosides, (e.g., $C_6$-$C_{14}$ alkyl maltosides), particularly n-alkyl-β-maltosides (more specifically, n-dodecyl-β-glucoside); and alkyl dimethyl amine oxides (e.g., ($C_6$-$C_{14}$) alkyldimethyl amine oxides, particularly lauryldimethyl amine oxide). Dialyzable, non-denaturing surfactants for use in a given application with a given protein can be readily identified employing well-known methods.

The term protein is used herein as broadly as it is in the art to refer to molecules of one or more polypeptide chains which may be linked to each other by one or more disulfide bonds. Proteins include glycoproteins (proteins linked to one or more carbohydrates), lipoproteins (proteins linked to one or more lipids), metalloproteins (proteins linked to one or more metal ions) and nucleoproteins (proteins linked to one or more nucleic acids). The term protein is however intended to exclude small peptides, such as those having less than 50 amino acids. The term protein includes polypeptides having 50 or more amino acids. A protein may comprise one or more subunits and the subunits may be the same or different. For example, a protein may be a homodimer (having two subunits that are the same) or a heterodimer (having two subunits that are different). Proteins typically have one or more biological functions. Proteins include enzymes which catalyze reactions and antibodies, transport proteins, receptor proteins or other proteins which bind to other chemical species (peptides, nucleic acids, carbohydrates, lipids, other proteins, antigens, haptens, etc.). Proteins useful in sensing compositions include soluble proteins, membrane proteins and transmembrane proteins. Soluble proteins are of particular interest for the formation of carbon nanotube/protein complexes.

The term polypeptide is used to refer to peptides having 20 or more amino acids and in particular. Peptides such as those reported in WO 03/102020, which is incorporated by reference in its entirety, are optionally excluded from the meaning of the term polypeptide as used herein.

Useful proteins include those that exhibit selective binding to given chemical species or, which are one member of a set (particularly a pair) of binding partners (e.g., avidin and biotin, a receptor and a receptor ligand, or an antibody or antibody fragment and an antigen to which it binds). In specific embodiments, useful proteins include soluble receptors and cell surface receptors. In other specific embodiments, useful proteins include G-protein coupled receptors (GPCRs). In more specific embodiments, useful proteins include steroid receptors, particularly estrogen receptors.

In some embodiments, proteins useful in sensing compositions may contain one or more of the carbon nanotube binding sequences disclosed in WO 03/102020, but in other embodiments, proteins useful in sensing compositions do not contain any one or more of the carbon nanotube binding sequences disclosed in WO 03/102020.

Enzymes function by binding to a substrate and catalyze a reaction of the substrate. Substrate selectivity or specificity of an enzyme is, at least in part, determined by the selectivity or specificity with which the enzyme binds to a substrate. Enzymes include among others those that catalyze oxidation and/or reduction reactions and those that catalyze cleavage of certain bonds or the formation of certain bonds. It is understood in the art that enzyme function may require the presence of cofactors and/or co-enzymes. Further, it is understood in the art that enzyme function may be affected by pH, ionic strength, temperature or the presence of inhibitors. Methods and devices as described herein can employ enzymes which are well-known in the art so that the requirements for any co-factors and/or co-enzymes and the effect of pH, ionic strength, temperature and other environmental factors as well as potential inhibitors will also be well-known. Enzymes useful in sensing compositions include oxidases, dehydrogenases, esterases, oxigenases, lipases, and kinases, among others which may be obtained from various sources. More specifically, enzymes useful in analyte sensing compositions include glucose oxidases, glucose dehydrogenases, galactose oxidases, glutamate oxidases, L-amino acid oxidases, D-amino acid oxidases, cholesterol oxidases, cholesterol esterases, choline oxidases, lipoxigenases, lipoprotein lipases, glycerol kinases, glycerol-3-phosphate oxidases, lactate oxidases, lactate dehydrogenases, pyruvate oxidases, alcohol oxidases, bilirubin oxidases, sarcosine oxidases, uricases, and xanthine oxidases and wherein the analyte is a substrate for the enzyme.

Proteins useful in sensing compositions may be truncations, variants, derivatives, or semi-synthetic analogs of a naturally-occurring protein which, for example, has been modified by modification of one or more amino acids to exhibit altered biological function, e.g., altered binding, compared to the naturally-occurring protein, is a deglycosylated form of a naturally-occurring protein or a variant or derivative thereof, or has glycosylation different than that of a naturally-occurring protein. Proteins as well as protein truncations, variants, fusions, derivatives or semi-synthetic analogs of naturally-occurring proteins and enzymes, exhibit a biological function that can be used detect an analyte. Protein truncations, variants, fusions, derivatives or semi-synthetic analogs of naturally-occurring proteins and enzymes may exhibit altered binding affinity and/or altered biological function compared to naturally-occurring forms of the proteins. Protein truncations, for example, specifically include the soluble portion or portions of membrane or transmembrane proteins. Protein fusions, for example, specifically include fusions of the soluble portion or portions of membrane or transmembrane proteins with soluble carrier proteins (or polypeptides).

Enzymes useful in sensing compositions may be a truncation, variant, fusion, derivative, or semi-synthetic analog of a naturally-occurring enzyme which, for example, has been modified by modification of one or more amino acids to exhibit altered activity, e.g., enhanced activity, compared to the naturally-occurring enzyme, is a deglycosylated form of a naturally-occurring enzyme or a variant, fusion, or derivative thereof, has altered glycosylation than that of a naturally-occurring enzyme, is formed by reconstitution of an apo-enzyme with its required co-factor (e.g., FAD), is formed by reconstitution of an apo-enzyme with a derivatized co-factor. Enzyme variants, fusions, derivatives or semi-synthetic analogs of naturally-occurring enzymes may exhibit altered substrate specificity and/or altered enzyme kinetics compared to naturally-occurring forms of the enzyme.

The term antibody (or immunoglobulin) as used herein is intended to encompass its broadest use in the art and specifically refers to any protein or protein fragment(s) that function as an antibody and is specifically intended to include antibody fragments including, among others, Fab' fragments. Antibodies are proteins synthesized by an animal in response to a foreign substance (antigen or hapten) which exhibit specific binding affinity for the foreign substance. The term antibody includes both polyclonal and monoclonal antibodies. Polyclonal and monoclonal antibodies selective for a given antigen are readily available from commercial sources or can be routinely prepared using methods and materials that are well-known in the art. A monoclonal antibody preparation can be derived from techniques involving hybridomas and recombinant techniques. Various expression, preparation, and purification methodologies can be used as known in the art. For example, microbial expression of antibodies can be employed (e.g., see U.S. Pat. No. 5,648,237). Human, humanized, and other chimeric antibodies can be produced using methods well-known in the art.

Sensing compositions can include carbon nanotube complexes with polysaccharides, particularly sensing polysaccharides. The term polysaccharide is used generally herein to include polymers of any monosaccharide or combination of monosaccharides. A polysaccharide typically contains 20 or more monosaccharide units. Oligosaccharide containing less than 20 monosaccharide units can be used if they are found to complex with carbon nanotubes. For assays for monosaccharide analytes, polymers of the monosaccharide analyte (e.g., polymers of glucose for use in assays for glucose) may be used. Polysaccharides and oligosaccharides can be derivatized with one or more chemically selective groups or moieties to impart chemical selectively to the polysaccharide.

Sensing compositions can include carbon nanotube complexes with derivatized polymers that are not proteins, polysaccharides (or oligosaccharides) or other biological polymers such as polynucleotides. Polymers which complex to carbon nanotubes and are useful in sensing compositions and methods herein include polymers which are derivatized to contain one or more chemically selective groups or moieties which impart chemical selectively to the polymer. Polymers that can be usefully derivatized include poly(ethylene glycol), poly(vinyl alcohol), poly(vinyl chloride), (e.g., and copolymers thereof, and polysorbitan esters (e.g., polyoxyethylene sorbitan fatty acid esters.)

A sensing element for detecting an analyte can include a selectively porous container adapted for receiving and retaining the components of a sensing composition. The container is sufficiently porous to allow analyte to enter the container without allowing the functional components of the analyte sensing composition to exit the container. The sensing composition is dispersed in a liquid or solid material. Typical liquids are aqueous solutions which include solutions in which the majority component is water, but which may include alcohols, glycols and related water soluble materials that do not affect the ability of the sensing composition to detect or quantitate analyte. The sensing composition may be dispersed in a solid matrix. The matrix can be formed from various polymers, silica, quartz or other glass, ceramics and metals with the proviso that the metal matrix is insulated from the surface with a coating that preserved the optical properties of the carbon nanotube/sensing polymer complexes. The matrix can be formed from a combination of such solid materials. The matrix can also be a semi-solid material such as a gel or a paste. The matrix must be sufficiently porous to allow analyte to enter without loss of sensing composition components that are needed to analyte detection. The matrix must also be sufficiently optically thin or transparent to the excitation and emission to allow detection of analytes. A solid matrix with dispersed sensing composition can serve as a sensing element. In a preferred embodiment, the sensing element is an implantable container or matrix comprising sensing composition which is biocompatible. The term "biocompatible" is employed as broadly as the term is used in the art and in preferred embodiments for human or veterinary applications the term refers to materials that cause minimal irritation and/or allergic response on implantation. The term also preferably refers to materials in which biofouling of pores is minimized.

Sensing elements include those that are implantable in tissue. Such sensors may be affected by foreign body encapsulation and/or membrane biofouling of the sensor surface. Fibroblast encapsulation at the site of sensor element implantation has been reviewed and art-recognized solutions to this problem include administration of antigenic factors and anti-inflammatory pharmaceuticals at the site of implantation to promote neovascularization. A sensor surface may be biofouled as endothelial cells adhere and either block or in some cases consume analyte, thus decreasing the accuracy or otherwise decreasing or destroying the function of the sensor. Sensor architecture can play a significant role in exacerbating or ameliorating the biofouling problem. Biofouling can limit the flux of analyte to the sensor as cellular adhesion becomes more pronounced. Electrochemical sensors, which are the most widely employed for glucose detection, measure the flux of analyte (e.g., glucose) from a limiting membrane. Biofouling in such sensors can decrease the measured signal and is corrected only by frequent recalibration and eventually replacement is required. In contrast, optical sensors, measure the concentration of analyte at the sensor directly and fouling results in a delay in sensor response. A sensor that measures concentrations of analyte directly does not exhibit significant distortion of the measured analyte concentration until the sensor response rate becomes commensurate with the rate of change in the bulk. Implanted optical sensors will exhibit an increased stability and longer useful life on implantation compared to sensors which measure analyte flux such as electrochemical sensors.

FIG. 1 depicts a sensing system for detecting one or more analytes comprises one or more sensing elements (300) and a detector (310) for measuring an optical response of the complexes in the sensing solution. Any appropriate optical detector may be employed. The detector can include any and all necessary device elements for detecting light and converting the signal detected into a form appropriate for analysis or display. Detectors and device elements for any needed signal conversion, analysis and display are known in the art and readily available for use. It is noted that the sensing elements of the system may be remote from the detector. More specifically, the sensing system can include a source of electromagnetic radiation (305) to provide electromagnetic radiation (307) of appropriate wavelength for exciting luminescence (315) of the complexed carbon nanotube in the sensing composition which can be detected by the detector. Any known source appropriate for the sensor application can be employed including light emitting diodes, or lasers. It is noted that the excitation source may be remote from the sensor and may also be remote from the detector. In a specific embodiment, the detector and the excitation source may be combined in a single device. Those of ordinary skill in the art can select light sources and/or detectors appropriate for use in sensor systems in view of what is generally known in the art and the specific wavelengths or wavelength ranges in which the sensor is to operate.

Non-limiting examples of analytes that can be determined using the compositions and methods described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g., thyroid stimulating hormone (TSH), thyroxine (T4), luteinizing hormone (LH), follicle-stimulating hormones (FSH), testosterone, progesterone, human chorionic gonadotropin, estradiol; other proteins or peptides, e.g. troponin I, c-reactive protein, myoglobin, brain natriuretic protein, prostate specific antigen (PSA), free-PSA, complexed-PSA, pro-PSA, EPCA-2, PCADM-1, ABCA5, hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Analytes may be detected in a wide variety of sample types, including a liquid sample or solid sample, a biological fluid, an organism, a microorganism or medium containing a microorganism, an animal, a mammal, a human, a cell line or medium containing a cell line. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte. In some embodiments, one or more of the above-mentioned reagents is stored in a channel or chamber of a fluidic device prior to first use in order to perform a specific test or assay. In some embodiments, the sample can be cancer cells. In other embodiments, the sample can be fermentation cells, incubation cells, generation cells, or biofuel cells.

As used herein, the terms "determination" or "determining" generally refer to the analysis of a species or signal, for example, quantitatively or qualitatively (whether the species or signal is present and/or in what amount or concentration), and/or the detection of the presence or absence of the species or signals. "Determination" or "determining" may also refer to the analysis of an interaction between two or more species or signals, for example, quantitatively or qualitatively, and/or by detecting the presence or absence of the interaction. For example, the method may include the use of a device capable of producing a first, determinable signal (e.g., a reference signal), such as an electrical signal, an optical signal, or the like, in the absence of an analyte. The device may then be exposed to a sample suspected of containing an analyte, wherein the analyte, if present, may interact with one or more components of the device to cause a change in the signal produced by the device. Determination of the change in the signal may then determine the analyte.

Specific examples of determining a species or signal include, but are not limited to, determining the presence, absence, and/or concentration of a species, determining a value or a change in value of a wavelength or intensity of electromagnetic radiation (e.g., a photoluminescence emission), determining the temperature or a change in temperature of a composition, determining the pH or a change in pH of a composition, and the like.

In one embodiment, a sensing composition includes a complex of a SWNT with a sensing polymer which includes an organic polymer modified with analyte-binding protein. The modification can be non-covalent (e.g., a non-covalent association of the organic polymer with the analyte binding protein) or covalent (e.g., the organic polymer is covalently bound to the analyte binding protein). The organic polymer can be, e.g., a carboxylated poly(vinyl alcohol) (cPVA).

The analyte binding protein can be one that undergoes a substantial conformational change when binding the analyte. For example, members of the periplasmic binding protein family can undergo a substantial conformational change when binding an analyte. The analyte binding protein can be a monosaccharide binding protein, e.g., glucose binding protein (GBP). GBP is an example of a periplasmic binding protein that undergoes a substantial conformational change when binding an analyte.

Thus, the sensing polymer can be cPVA covalently modified with GBP. GBP is a periplasmic binding protein which binds glucose with a high degree of specificity. GBP exhibits equilibrium binding kinetics; in other words, glucose can be easily unbound from a glucose-GBP complex, thus providing for a reversible binding event. See, for example, U.S. Patent Application Publication no. 2010/0279421, which is incorporated by reference in its entirety.

High throughput analysis methods, where libraries of homologous molecules are screened and compared for efficacy, can be valuable for drug discovery and catalytic development. The application of high throughput analysis methods to the problem of optical sensor development can provide structural and chemical clues as to the most effective ways of transducing analyte binding to optically modulate SWNTs. For example, a library of boronic acid (BA) constructs to sodium cholate suspended SWNTs (SC/SWNTs) can be screened for their ability to modulate fluorescence emission in response to glucose. An examination of successful candidates can yield structural and chemical design rules to enable such sensors.

A boronic acid can be an excellent molecular receptor for saccharides. The detection and monitoring of saccharides (e.g., glucose and fructose) can be vital in medical diagnostics, biomedical research, and biotechnology. Boronic acids have attracted attention as an alternative receptor to enzymes for saccharide detection (e.g., glucose oxidases for glucose detection). The enzyme-based sensing has the disadvantages that since it is based on the rate of the reaction between the enzyme and the analyte, this approach can be sensitive to various factors that affect the enzyme activity and the mass transport of the analyte, it can consume the analyte, and it can require mediators; in contrast, the boronic acid-based sensing can be based on the reversible and equilibrium-based complexation of boronic acids and saccharides, thus consuming no analytes.

The reversible complexation of saccharides with aromatic boronic acids can produce a stable boronate anion, changing the electronic properties of the boronic acids, such as the reduction potential of aromatic boronic acids. This alternation in the electronic properties of aromatic boronic acids upon binding of saccharides has been a basic scheme for various boronic acid-based saccharide sensing approaches, including electrochemical, fluorescence, and colorimetric measurements. Thus, complexation of saccharides with aromatic boronic acids conjugated on the surface of SWNTs, for example, through π-π interactions between the graphene sidewall of SWNTs and the aromatic moiety of the boronic acids, can modulate the SWNT fluorescence signal in response to binding of saccharides.

In one embodiment, a sensing composition includes a complex of a SWNT with a sensing polymer which includes an organic polymer modified with a chemical moiety that is capable of reacting with an analyte. The modification can be non-covalent (e.g., a non-covalent association of the organic polymer with the reactive moiety) or covalent (e.g., the organic polymer is covalently bound to the reactive moiety). The reactive moiety can be a boronic acid, and the analyte can be a monosaccharide, e.g., glucose. The organic polymer can include diol groups, such that a boronic acid forms a boronate ester with the organic polymer. In this configuration, when analyte molecules are introduced to the system, they bind to the boronic acid, detaching it from the organic polymer. Thus the analyte competes with the organic polymer for the binding of the boronic acid; the fluorescence change resulting from the detachment of the boronic acid is used to measure the analyte. Alternatively, the organic polymer can be a surfactant (e.g., dextran, PVA, chitosan, alginate, and lipid PEG) modified such that the boronic acid is exposed toward the solution to facilitate binding with the analyte. In this configuration, the binding of analyte molecules to the boronic acid modulates the fluorescence of the SWNT. See, e.g., U.S. Patent Application Publication no. 2010/0279421, U.S. patent application Ser. No. 13/090,199, filed Apr. 19, 2011, and provisional application No. 61/325,599, filed Apr. 19, 2010, each of which is incorporated by reference in its entirety.

In another embodiment, a sensing composition includes a complex of a SWNT with a boronic acid (BA-SWNT complex). The fluorescence of BA-SWNT complexes, quenched by the attachment of boronic acids to nanotubes, can be selectively recovered in response to the binding of glucose in the physiological range of glucose concentrations. The reversible fluorescence quenching of the BA-SWNT complex that exploits boronic acids as a molecular receptor can provide SWNT-based highly stable and sensitive, nIR optical sensing of saccharides. The optical sensing of glucose holds promise for noninvasive in vivo continuous glucose monitoring, important for diabetes management. For instance, commercial noninvasive continuous glucose monitors for long-term use are not currently available. With the non-photobleaching, nIR fluorescence of SWNTs, the SWNT-based nIR optical sensing of glucose has great potential in this regard.

The modulation of SWNT fluorescence of SWNT through the binding of analyte molecules to boronic acid results from either (i) the shift of the peak wavelength or (ii) the change in the fluorescence intensity. Depending on the boronic acid used, the fluorescence intensity can be increased or decreased upon the binding of analyte molecules to a boronic acid-SWNT sensor. For example, when using 4-chlorophenylboronic acid, the fluorescence intensity can decrease in the presence of glucose. In contrast, the fluorescence intensity of the sensor can increase upon exposure to glucose when using 4-cyanophenylboronic acid (see FIGS. 8A-8C). The shift of the peak and/or the change of the fluorescence intensity can thus be used to measure an analyte. Glucose recognition and transduction can be facilitated by para-substituted, electron withdrawing phenyl boronic acids that are sufficiently hydrophobic as to adsorb to the nanotube surface.

In another embodiment, a sensing composition can be encapsulated in a microparticle, e.g., a hydrogel microparticle. The microparticle can be biocompatible and of an injectable size, e.g., 50 to 500 µm. The hydrogel microparticle can have a microbead structure or a core-shell structure. In a microbead structure, the microbeads contain the sensing composition dispersed in the hydrogel structures. In a core-shell (or microcapsule) structure, the microparticle includes an aqueous core solution of the sensing composition (e.g., in PBS), and the hydrogel shell surrounding the aqueous core solution. Various biocompatible hydrogels, such as alginate, PEG, and chitosan, can be used for both the microbeads and the core-shell microparticles. The hydrogel microparticles confine and protect the sensing composition, while allowing analytes (e.g., glucose) to freely diffuse into and out of the hydrogel microparticles. These hydrogel microparticles can be subcutaneously implanted with minimal invasiveness, and reduce biofouling, which is favorable for long-term, accurate biosensor performance. The hydrogel microparticles can be produced using commercially available encapsulating systems (e.g., encapsulating systems from Inotech and Nisco) and flow-focusing microfluidic devices.

EXAMPLES

Example 1: GBP-SWNT Glucose Sensor

Periplasmic binding proteins (PBPs) are non-enzymatic receptors found in bacteria. They play a role in the transport of small molecules such as carbohydrates, amino acids, vitamins, and ions. Importantly, most PBPs can adopt two distinct conformations, referred to as open and closed forms. The transition between the open and closed forms is determined by binding of a specific ligand. The closed conformation predominates in when the ligand is bound to the PBP. This transition between the two conformations provides a mechanical action, which motivates their use as nanoscale actuators. While PBPs have been incorporated into electrochemical sensors extensively, and used to induce a fluorescence resonance energy transfer response to grafted donor/ acceptor fluorophores to their surface, PBPs remain unexplored as direct actuators of nanoscale devices. One of the notable PBPs is glucose-binding protein (GBP), is a monomeric protein capable of recognizing glucose (β-D-glucose) with a high affinity. GBP has a bilobate structure of two main domains linked by three peptide segments that act as a hinge. The glucose-binding site is located in the cleft between the two domains. GBP also undergoes a sizable change in conformation upon glucose binding to initiate a signal transduction. See, e.g., Yoon, H., et al., *Angewandte Chemie*, 2011, 50, 1828-1831, and the associated Supporting Information, each of which is incorporated by reference in its entirety, and references cited therein.

Materials and Methods

Synthesis of cPVA. PVA (Aldrich 13,000-23,000 molecular weight, 30 mg mL$^{-1}$) was reacted with dimethylaminopyridine (21.5 mM) and succinic anhydride (21.5 mM) in N-methylpyrrolidone at 60° C. for 24 h. The resulting product was thoroughly washed with isopropyl alcohol to remove residual reagents and then allowed to dry in a vacuum oven at room temperature. Attenuated total reflection-infrared spectroscopy (using a Thermo Nicolet 4700 spectrometer) was conducted to characterize the final product. After the carboxylation, a new absorption peak was observed at 1670 cm$^{-1}$, attributed to the carbonyl stretching of the carboxyl group.

Fabrication of GBP-cPVA/SWNT. CoMoCAT SWNT (Aldrich, 0.5 mg mL$^{-1}$) was immersed in a 2 wt % aqueous sodium cholate solution and then the mixture was ultrasonicated for 1 h at a power of 10 W. The resulting black solution was centrifuged to separate impurities, including unstable nanotube bundles, and the upper 80% of supernatant was retrieved as a stable suspension of sodium cholate-SWNT. Subsequently, aqueous cPVA (10 wt %) solution was mixed with the sodium cholate-SWNT solution in a 1:1 ratio by volume. The cPVA displaced the sodium cholate on the nanotube surface and the free sodium cholate was eliminated by dialysis in distilled water. The cPVA/SWNT exhibited no aggregation during dialysis in distilled water without any stabilizers, demonstrating that cPVA provided enough colloidal stability to individual SWNT. The GBP was covalently attached to cPVA/SWNT using a coupling chemistry, in which N-(3-dimethylaminopropyl)-N'-ethylcarbodiimide (EDC) and N-hydroxysuccinimide (NHS) were employed. EDC/NHS was dissolved in PBS at a concentration of 40/40 mol per PBS volume (mL). The cPVA/SWNT was mixed with the EDC/NHS solution at a 1:1 volume ratio to activate the carboxyl groups for 2 h. Subsequently, excess EDC/NHS was removed using a centrifugal filter with additional PBS. Finally, the activated cPVA/SWNT solution was mixed with GBP solution at a 2:3 volume ratio to yield GBP-cPVA/ SWNT that was suspended in PBS. The final concentration of SWNT was approximately 2.1 mg L$^{-1}$.

Fluorescence measurements. SWNT fluorescence spectra were measured using a home-built NIR photoluminescence measurement setup, where a Zeiss AxioVision inverted microscope was coupled to a Princeton Instruments InGaAs OMA V array detector through a PI-Action SP2500 spectrometer. The fluorescence images were recorded also using a home-built NIR photoluminescence microscope (Carl Zeiss, Axiovert 200), with a charge-coupled device (CCD) camera (Carl Zeiss, ZxioCamMRm) and InGaAs OMA 2D array. Movies were acquired at 1 s/frame using the WinSpec data acquisition program (Princeton Instruments). The spectrum and image were obtained using 785 nm and 658 nm laser excitation sources.

Other analyses. AFM images were taken using an Asylum Research MFP-3D atomic force microscope. Photo-absorption measurements were carried out using a Shimadzu UV-3101PC UV-VIS-NIR scanning spectrophotometer in a cuvette with a 1 cm path length. The data of single-nanotube measurement was processed using ImageJ software with Time Series Analyzer plugin. The obtained trace was fitted with a hidden Markov algorithm. Single-particle tracking was conducted using ImageJ software with Particle Tracker Plugin.

Preparation of SWNT Suspensions and BA-SWNT Complex Solutions.

SWNTs synthesized by the CoMoCAT process (Sigma-Aldrich, 0.5 mg/ml) were sonicated in a 2% aqueous solution of sodium cholate (SC) for 20 minutes using a 750-W cup-horn sonicator (Vibra-Cell) at 90% amplitude. The SWNT suspension was ultracentrifuged at 30,000 rpm for 4 hours, and the upper 80% of nanotube suspension was retrieved as a stable aqueous suspension of individual SWNTs functionalized by SC(SC/SWNTs). BA-SWNT complex solutions were prepared by adding boronic acids dissolved in DMSO (1 M) into the SC/SWNT solutions.

Spectroscopy.

Near-infrared (nIR) fluorescence spectra were acquired with 785-nm excitation using a Zeiss AxioVision inverted microscope coupled to a Princeton Instruments InGaAs OMA V array detector through a PI Action SP 2500 spectrometer. Absorbance was measured using a Shimadzu UV-3101PC UV-visible-111R scanning spectrophotometer in a cuvette with a 1-cm pathlength.

High Throughput Screening.

High throughput screening of 30 boronic acids and the response of the 30 BA-SWNT complexes to glucose was done in a 96-well plate. The 30 BA-SWNT complex solutions were prepared by adding 10 µL of 30 boronic acids in DMSO (1 M) to 190 µL SC/SWNT solutions. The fluorescence spectrum of the BA-SWNT complex solutions was measured 30 minutes after adding boronic acids. The fluorescence spectral response of the BA-SWNT complexes to glucose (50 mM) was measured 30 minutes after adding 10.5 µl, of glucose (1 M) to the BA-SWNT complex solutions. The equal volume of boronic acids (10 µL) and glucose (10.5 µL) was added to each well of SC/SWNT solutions (190 µL). The SWNT solutions were thoroughly mixed after adding boronic acids and glucose. The solutions reached the equilibrium within several minutes after adding boronic acids and glucose. The BA-SWNT complexes and the effects of glucose were stable for at least several hours.

Results and Discussion

Figure 2:
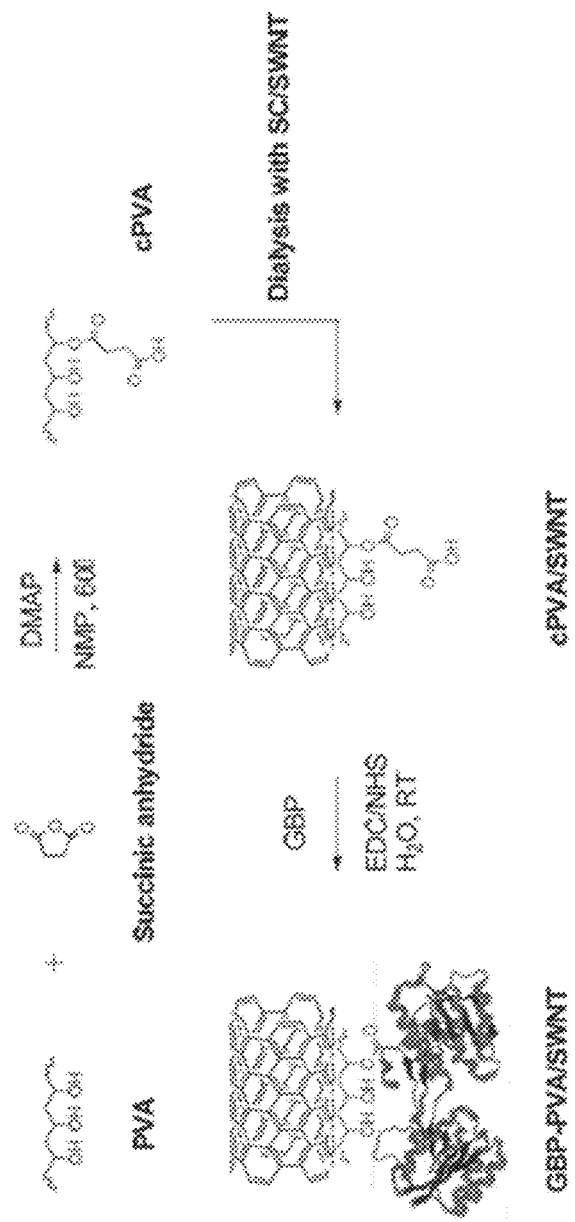
FIG. 2 is a schematic depiction of the synthetic steps for the fabrication of GBP-cPVA/SWNT. Abbreviations: DMAP, dimethylaminopyridine; NMP, N-methylpyrrolidone; SC, sodium cholate; EDC, N-(3-dimethylaminopropyl)-N'-ethylcarbodiimide; NHS, N-hydroxysuccinimide. SWNT were first dispersed in an aqueous sodium cholate solution. PVA was carboxylated via an esterification reaction with succinic anhydride and dimethylaminopyridine, and the cPVA was then used to colloidally disperse SWNTs, via dialysis to remove sodium cholate in the presence of the polymer. The resulting cPVA/SWNT remained stable over months with well-defined absorption and fluorescence observed after suspension.

As illustrated schematically in FIG. 2, GBP was covalently conjugated to carboxylated poly(vinyl alcohol)-wrapped SWNTs (cPVA/SWNTs). The resulting GBP-cPVA/SWNT sensing composition provided allosterically controlled optical transduction in response to glucose.

GBP was heterologously expressed in *E. coli*, and SWNTs were colloidally dispersed with carboxylated PVA (cPVA) (see, e.g., Yoon, H., et al., *Angewandte Chemie*, 2011, 50, 1828-1831, and the associated Supporting Information, each of which is incorporated by reference in its entirety). Carboxy groups on the cPVA/SWNT complex were used to attach the protein, through amine coupling to lysine residues on the GBP. These complexes demonstrated a reversible fluorescence quenching in response to glucose, as described below.

Figure 3A:
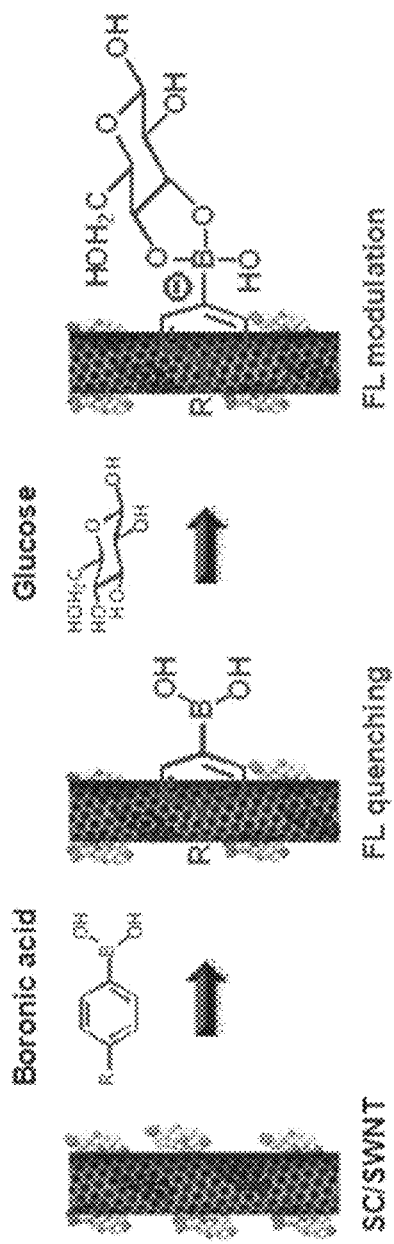
FIG. 3A is a schematic depiction of the reaction of boronic acids with sodium cholate suspended SWNTs (SC/SWNTs) and the fluorescence (FL) spectral response of the boronic acid-SWNT complex to glucose.

FIG. 3A illustrates a mode by which an aromatic boronic acid can alter the fluorescence spectral response of boronic acid-SWNT (BA-SWNT) complexes to a substrate, such as glucose in aqueous solutions.

Figure 3B:
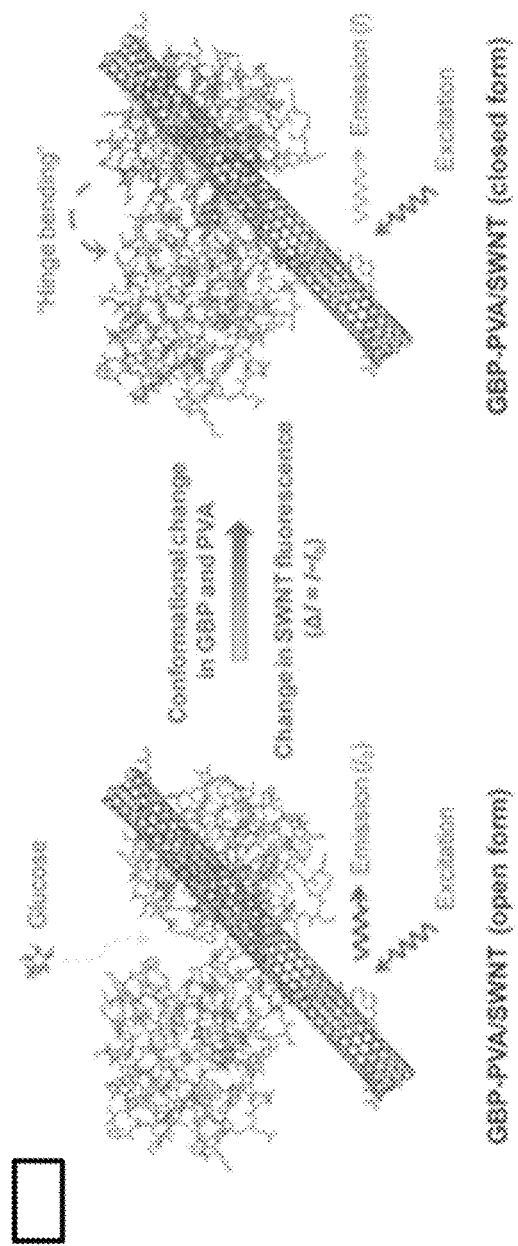
FIG. 3B is a schematic depiction of glucose recognition in the GBP-cPVA/SWNT conjugate.
Figure 3C:
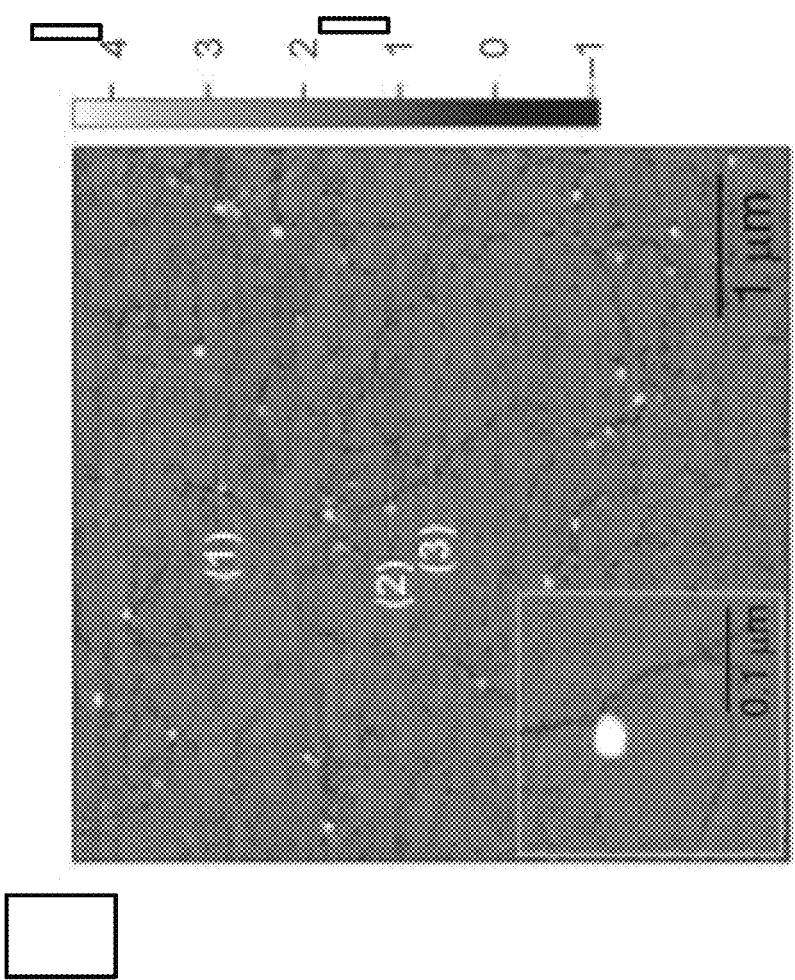
FIG. 3C is an AFM image (left bottom inset: a high magnification image) of GBP-cPVA/SWNTs.
Figure 3D:
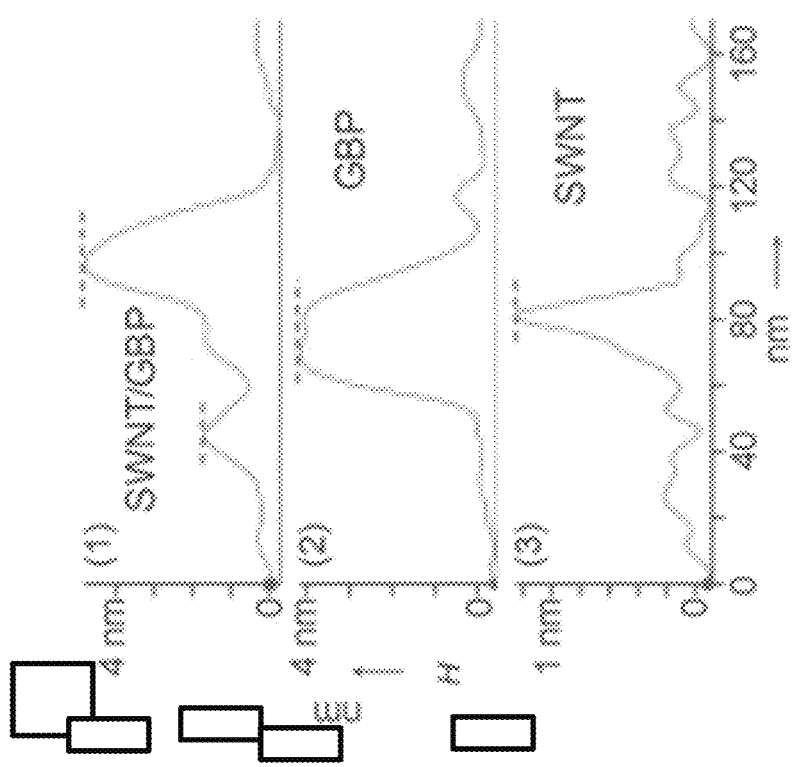
FIG. 3D is a graph depicting height information obtained from the AFM image: (1) SWNT and GBP; (2) GBP; (3) SWNT.
Figure 3E:
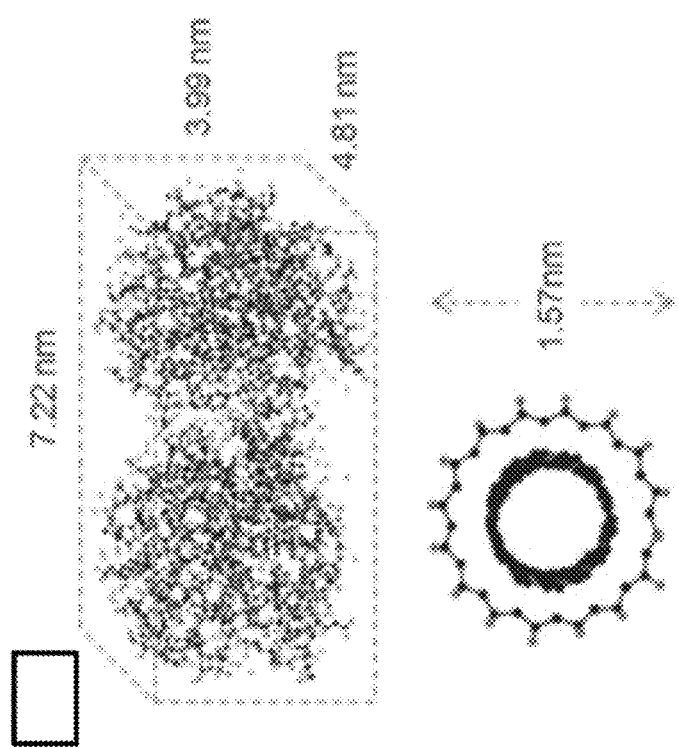
FIG. 3E schematically illustrates the dimensions of GBP (top, perspective view) and cPVA/SWNT (bottom, cross-sectional view) calculated from the minimum-energy configuration.

FIG. 3B illustrates schematically the structure of the GBP-cPVA/SWNT conjugate. The hinge bending action associated with glucose recognition is believed to modulate the fluorescence of the SWNT (see, e.g., M. J. Borrok, et al., *Protein Sci.* 2007, 16, 1032, which is incorporated by reference in its entirety). Atomic force microscopy (AFM) was carried out in tapping mode to characterize the structure of GBP-cPVA/SWNTs (see FIG. 3C). Globular species 4 nm in size (white dots) were observed bound to fibrillar structures of 1 nm average height, as expected. These dimensions are consistent with those of GBP and cPVA-wrapped SWNTs (see FIGS. 3D-3E). From a collection of such AFM images and optical spectroscopy, it was concluded that the majority of complexes include a single SWNT with GBP attached to the sidewall. Binding of GBP to cPVA/SWNT was further confirmed by gel electrophoresis, Bradford assay, infrared spectroscopy, and fluorescence spectroscopy.

Figure 4:
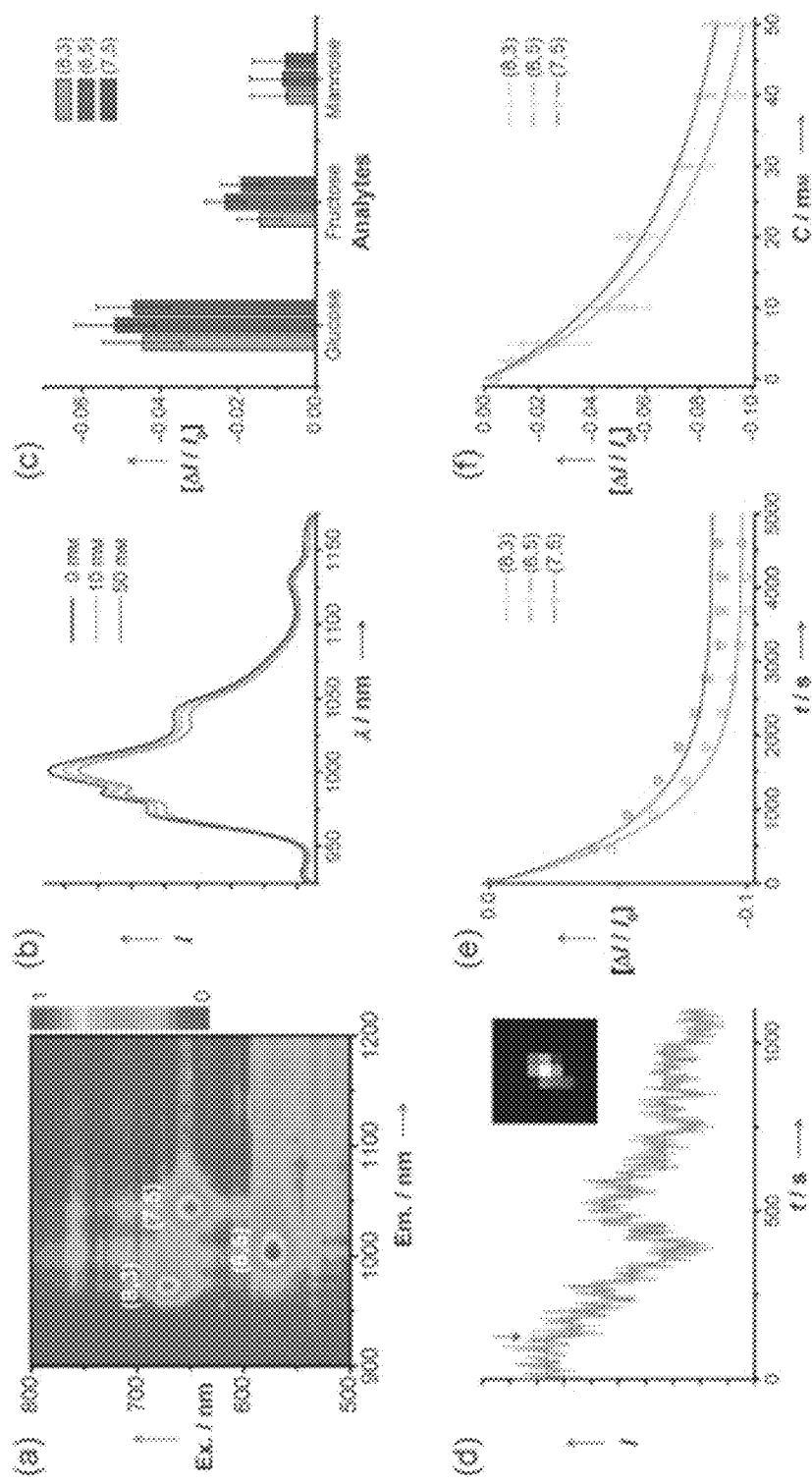
FIG. 4A shows a fluorescence profile (excitation vs. emission) of GBP-cPVA/SWNTs; the intensity was normalized with the maximum.
FIG. 4B presents typical fluorescence spectra of GBP-cPVA/SWNTs before and after glucose introduction ($\lambda_{exc}$=785 nm).
FIG. 4C is a histogram showing the selectivity of GBP-cPVA/SWNTs (at 10 mM sugar).
FIG. 4D shows a NIR fluorescence image (inset, each pixel is 0.5×0.5 µm) and spatially integrated intensity trace for single GBP-cPVA/SWNT conjugate recorded in the presence of 10 mM glucose ($\lambda_{exc}$=658 nm). The arrow indicates the addition of glucose. Intensity variations (lighter gray) were fitted by a hidden Markov model (darker gray).
FIG. 4E illustrates real-time responses of GBP-cPVA/SWNTs upon addition of 50 mM glucose ($\lambda_{exc}$=785 nm).
FIG. 4F shows calibration curves for GBP-cPVA/SWNTs. The experimental and calculated data are plotted by symbols and lines, respectively.

The excitation-emission profile of GBP-cPVA/SWNTs was measured FIG. 4A, showing expected fluorescence peaks originating from three nanotube species, (8,3), (6,5), and (7,5). It was concluded that cPVA itself had little effect on nanotube fluorescence and that the SWNTs were individually suspended. Emission spectra of GBP-cPVA/SWNTs were also measured in the presence of glucose (FIG. 4B) demonstrating an approximately uniform decrease. The peaks at 973 nm, 1001 nm, and 1041 nm were assigned to the (8,3), (6,5), and (7,5) nanotubes, respectively; while the peak at 986 nm was attributed to the 2-phonon G' Raman peak typical of graphene structures. See, e.g., Choi, J. H., et al., *Nano Lett.* 2007, 7, 861, which is incorporated by reference in its entirety. The response was found to be highly selective to glucose, as expected (FIG. 4C) since GBP is known to have a high selectivity toward glucose over fructose and mannose. The mechanism was found to be an exciton quenching after photoabsorption, as the absorption spectrum remained unchanged under the same conditions. GBP-cPVA/SWNT conjugates were deposited on a glass substrate and each nanotube was imaged as a bright near-IR pixel cluster that allowed for independent monitoring. FIG. 4D exhibits the integrated intensity trace for a single GBP-cPVA/SWNT conjugate in the presence of glucose, added at time 120 s. The fluorescence of the single protein-nanotube conjugate showed quantized blinking associated with stochastic quenching of excitons from adsorption of a quenching entity. In this case, these fluctuations correspond to quenched and dequenched states caused by the GBP, as demonstrated previously for $H_2O_2$ (see, for example, Jin, H., et al., *Nano Lett.* 2008, 8, 4299; and Jin, H., et al., *Nat. Nanotechnol.* 2010, 5, 302, each of which is incorporated by reference in its entirety). This result clearly demonstrated that the quenching mechanism in response to glucose involved a single nanotube, and an aggregation step, which was consistent with the above observations.

Changes in the emission from GBP-cPVA/SWNTs were systematically investigated at different concentrations of glucose to evaluate the effective affinity towards glucose and the dynamics of actuation. The emission intensity could be monitored consistently over a long observation time (>60 h) due to the photostability of SWNT. FIG. 4E describes typical transient responses of GBP-cPVA/SWNTs upon glucose addition. The emission intensity decreased before reaching equilibrium over a range of glucose concentrations (2.5 mM to 50 mM). A calibration curve was be generated from this equilibrium quenching response (FIG. 4F) and generally demonstrated linear behavior at low concentrations, with nonlinearity above 10 mM. The responses were similar for all three nanotube species with slightly different sensitivities. No response was observed from a cPVA/SWNT control that lacked GBP.

A simple kinetic model described both the transient and equilibrium behavior of GBP-cPVA/SWNTs. Since the response was clearly reversible, a reversible binding mechanism was proposed whereby GBP, in response to glucose, actuated the SWNT. Hence, the glucose-GBP binding reaction can be described by:

   [1]

where GBP* represents the GBP bound with glucose. The rate equation for the above reaction is $$\frac{d[GBP^*]}{dt} = k_f[\text{Glucose}][GBP] - k_r[GBP^*] \quad [2]$$

where $k_f$ and $k_r$ are constants for [Glucose]>>total protein concentration ($O_r$). The following equation is derived by integrating Equation (2):

$$[GBP^*(t)] = \frac{[\text{Glucose}]K_{eq}\theta_T\left\{1 - e^{-\left([\text{Glucose}]k_f + \frac{k_r}{K_{eq}}\right)t}\right\}}{1 + [\text{Glucose}]K_{eq}} \quad [3]$$

In this equation, $K_{eq}$ is the equilibrium binding constant for glucose and protein. The [GBP*(t)] directly affects the fluorescence intensity of the SWNT and thus it can be correlated with the change in emission intensity:

$$\frac{\Delta I}{I_0}(t) = -A\frac{[GBP^*(t)]}{\theta_T} \quad (4)$$

Here, A is a proportionality factor scaling the response. In the case of t→∞ (steady state), $K_{eq}$ and A are calculated from the initial slope of the calibration curve. The $K_{eq}$ measures the ability of GBP to bind glucose, which is extrinsically influenced by the open or closed status of the GBP attachment. While suitable covalent immobilization of GBP makes it more stable, excessive covalent bonding can lead to the partial degradation and damage of the protein. The $K_{eq}$ measured here, which were considerably lower than that of free, untethered GBP (ca. $10^6$ $M^{-1}$), make the GBP-cPVA/SWNT suitable for recognizing glucose in the physiological concentration range of 2 mM to 30 mM. The agreement between the model and experimental data supported the reversible binding mechanism asserted above.

Figure 5:
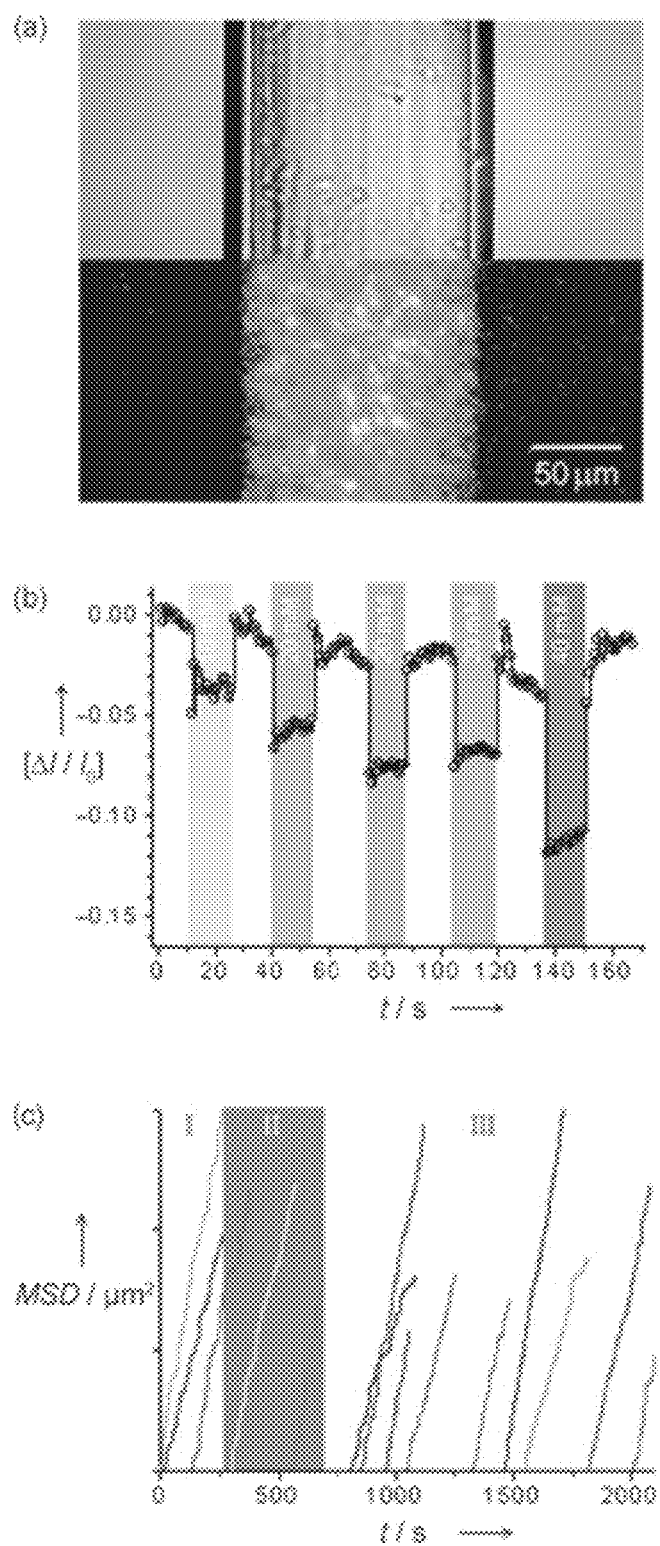
FIG. 5A shows optical (top) and near-infrared fluorescent (bottom) images ($\lambda_{exc}$=658 nm) of a dialysis microcapillary containing GBP-cPVA/SWNT solution; for clarity, the fluorescent image was colored green.
FIG. 5B shows the response curve of the encapsulated GBP-cPVA/SWNTs upon cyclic exposure to glucose ($\lambda_{exc}$=785 nm); the spectra were acquired at 10 s/frame and the (6,5) peak intensity trace was calculated from the collected spectra. The gray-colored region indicates the presence of glucose.
FIG. 5C presents examples of MSD curves for three time sections: I) no glucose-GBP interaction; II) glucose-GBP binding; and III) glucose-GBP unbinding.

GBP-cPVA/SWNTs were encapsulated in a dialysis microcapillary (FIG. 5A; 200 µm inner diameter, 13 kDa molecular weight cutoff) to provide more insight into the glucose-GBP interaction on the cPVA/SWNT. The dialysis microcapillary allowed diffusion of solutes, which were below the molecular weight cutoff, in and out of the encapsulated solution volume. The lower panel of FIG. 5A shows a NIR fluorescence image of the GBP-cPVA/SWNT solution and the surrounding medium which were compartmentalized by the dialysis membrane. The reversibility of the GBP-cPVA/SWNT was easily explored in this configuration. See, for example, P. W. Barone, et al., *Nat. Mater.* 2005, 4, 86; P. W. Barone, et al., *Anal. Chem.* 2005, 77, 7556; and P. W. Barone, et al., *Acs Nano* 2009, 3, 3869, each of which is incorporated by reference in its entirety. Upon periodic exposure to glucose, as shown in FIG. 5B, the encapsulated GBP-c/SWNT had a reversible modulation in fluorescence intensity. This result also confirmed the reversibility of the mechanism. Reversible response is one of the requirements for continuous monitoring of analytes in certain sensing applications.

Confining the GBP-cPVA/SWNT sensing composition in the microcapillary also offered an opportunity to explore the diffusion of the sensing composition during the glucose-GBP interaction. Real-time NIR emission from the encapsulated GBP-cPVA/SWNT composition was recorded in a one frame-per-second movie, and then a single-particle tracking technique was employed to analyze the individual particle displacements and map out the individual trajectories. Numerous nanotube trajectories (ca. 80,000) were collected to inspect minute dynamic variations involved in the glucose-GBP binding/unbinding events. Each trajectory was numerically analyzed using a standard mean-square displacement (MSD) method to identify its diffusion mode. FIG. 5C displays representative plots of MSD versus time for the three conditions during the measurement: I) no glucose-GBP interaction; II) glucose-GBP binding; III) glucose-GBP unbinding. Glucose (50 mM) was added at frame 250 and then removed at frame 650 during the course of the movie. The majority of the MSD curves were linear, which indicated that the nanotube conjugates were subject to normal Brownian diffusion in all conditions. This observation implied the following: 1) there was no interparticle aggregation that could have induced a decrease in fluorescence intensity during the measurement; 2) the GBP-cPVA/SWNTs had high colloidal stability during the microdialysis, which allowed continuous monitoring of the reversible binding event.

The accuracy of the system in measuring glucose concentrations was tested with reference to a Clarke error grid, which can be used to determine both the accuracy and the suitability of glucose sensors for use by patients. In these grids, the measured glucose concentration is plotted versus the actual glucose concentration to give a series of data points. If the data point falls in region A, the reading is within ~20% of the actual glucose concentration; in region B, the reading is more than 20% off of the actual glucose concentration, but would not lead to inappropriate action on the part of the patient. Data in region C indicate readings that would lead to unnecessary treatment, but not in a way that seriously jeopardizes the patient. Data falling in region D represent failures to detect hypoglycemia and hyperglycemia and would therefore lead to an inappropriate lack of treatment. Finally, data falling in region E represent sensor readings which would lead the patient to confuse hypoglycemia for hyperglycemia, or hyperglycemia for hyperglycemia. As a result, the action taken by the patient would be potentially very harmful or even fatal.

The results of glucose measurements using a GBP-cPVA/SWNT sensor in human blood serum were plotted on a Clarke Error Grid. The sensor performed very well at blood glucose concentrations of over 300 mg/dl (≥15 mM), but was less accurate in the very low glucose concentration regime (below 150 mg/dl or <8 mM).

Example 2: Boronic Acid-Conjugated SWNT Glucose Sensor

The fluorescence response of SWNT dispersed with sodium cholate (SC/SWNT) to various boronic acids at 50 mM concentration was measured. The SC/SWNT solution was prepared as described above: (i) CoMoCAT SWNT (Aldrich, 0.5 mg $mL^{-1}$) was immersed in a 2 wt % aqueous sodium cholate solution and then the mixture was ultrasonicated for 1 h at a power of 10 W and (ii) the resulting black solution was centrifuged to separate impurities, including unstable nanotube bundles, and the upper 80% of supernatant was retrieved as a stable suspension of sodium cholate-SWNT. Boronic acid solutions (~1 M) were prepared by dissolving the boronic acids (listed in Table 1 below) in dimethyl sulfoxide. The boronic acid solutions (~1 M) were then added into samples of the SC/SWNT solution. The fluorescence spectrum of each SC/SWNT solution was measured before and after adding the boronic acid solutions (30 minutes after adding the boronic acid solutions) using a home-built NIR photoluminescence measurement setup (a Zeiss AxioVision inverted microscope coupled to a Princeton Instruments InGaAs OMA V array detector through a PI-Action SP2500 spectrometer).

Figure 6:
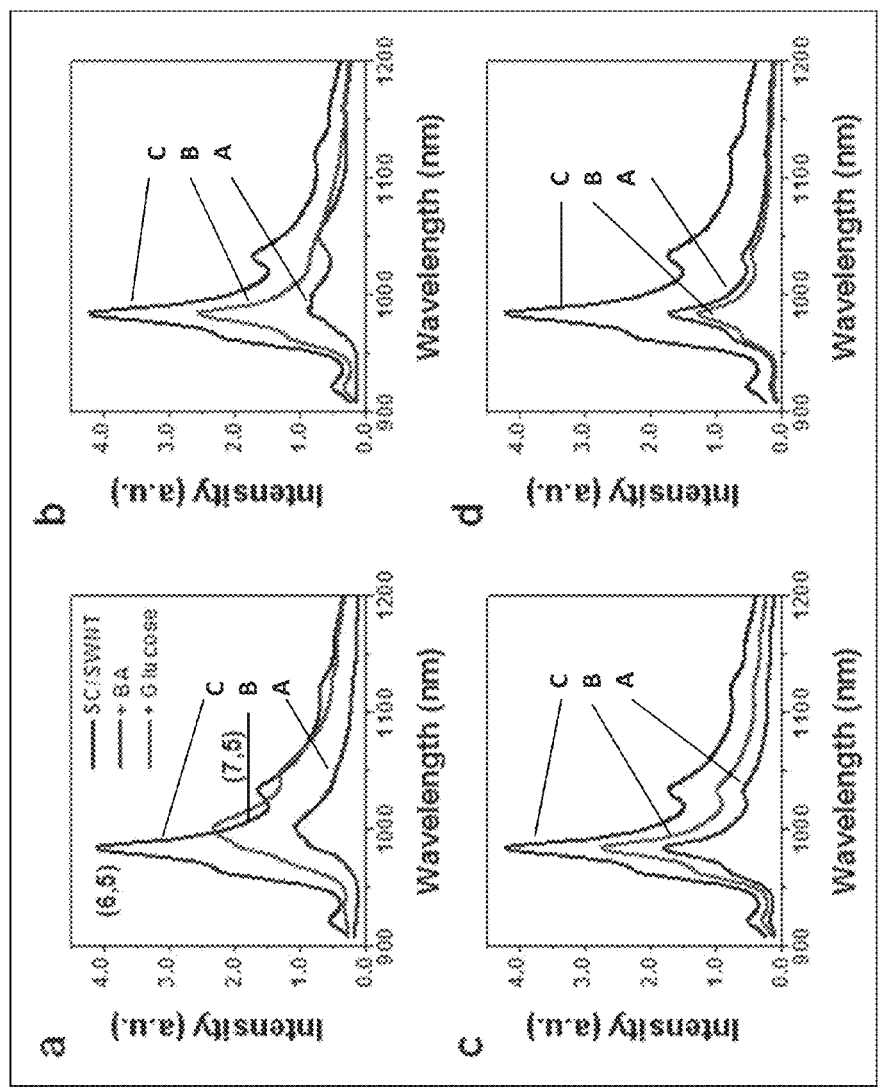
FIG. 6 shows representative fluorescence spectra that compare the original spectrum of SC/SWNTs (C), the spectrum after adding 50 mM boronic acids to SC/SWNT solutions (A), and the spectrum after adding 50 mM glucose to the BA-SWNT complex solutions (B). The BA-SWNT complexes were prepared with 4-chlorophenylboronic acid (BA2) (a), 4-cyanophenylboronic acid (BA9) (b), 9,9-dihexylfluorene-2,7-diboronic acid (BA16) (c), and indazole-6-boronic acid (BA30) (d).

FIG. 6 shows representative fluorescence spectra that compare the original spectrum of SC/SWNTs (Line C), the spectrum after adding 50 mM boronic acids to the SC/SWNT solutions (Line A), and the spectrum after adding 50 mM glucose to the BA-SWNT complex solutions (Line B). The addition of boronic acids resulted in a fluorescence loss and/or an emission wavelength shift of SWNT fluorescence (A lines in FIG. 6): the BA-SWNT complex of 4-chlorophenylboronic acid (BA2) and 4-cyanophenylboronic acid (BA9) shows both the fluorescence loss and the red-shift of the emission wavelength, whereas the BA-SWNT complex of 9,9-dihexylfluorene-2,7-diboronic acid (BA16) and indazole-6-boronic acid (BA30) only shows the fluorescence loss. The subsequent addition of a model analyte (glucose in our study) to the BA-SWNT complex solutions also caused a fluorescence intensity change (Lines B in FIG. 6): the nanotube fluorescence either recovered (BA2, BA9, and BA16) or further decreased (BA30). The fluorescence recovery of the BA-SWNT complex of 4-cyanophenylboronic acid (BA9) upon introduction of glucose also accompanied a blue-shift of the emission wavelength (FIG. 6b). This wavelength shift, or solavtochromism was generally rare among SWNT optical responses to molecular binding.

Figure 7:
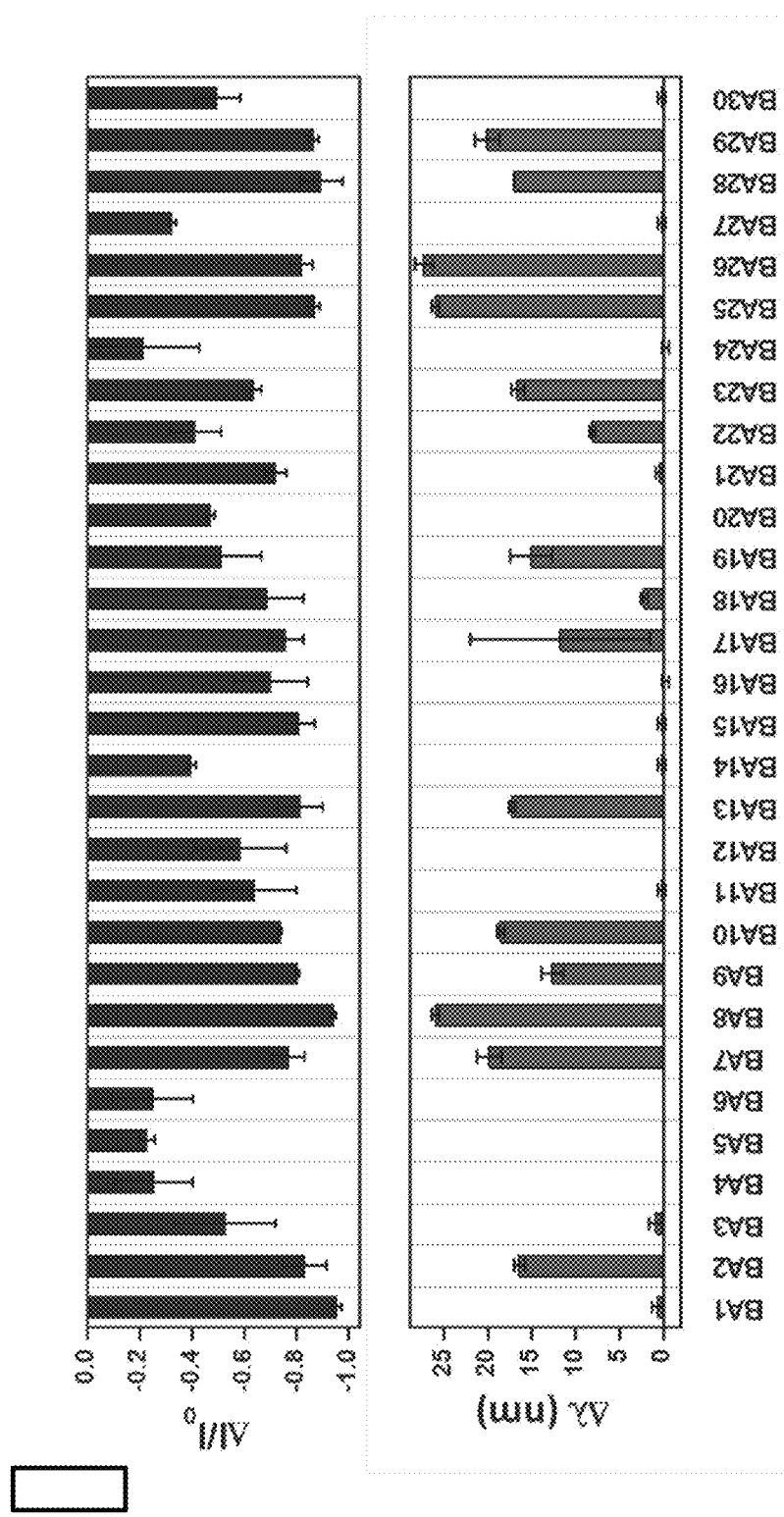
FIG. 7 are graphs summarizing the relative change in fluorescence intensity (top panel) and shift in peak fluorescence wavelength (lower panel) for sodium cholate-dispersed SWNTs when exposed to various boronic acids.

The results are summarized in FIG. 7; the top panel shows the relative change in fluorescence intensity ($\Delta I=I-I_0$, where I is the peak fluorescence intensity of SWNT and $I_0$ is the initial peak fluorescence intensity) for the boronic acids listed in Table 1; the lower panel shows the difference (shift), in nm, between the position of the peak fluorescence wavelength in the absence and presence of the various boronic acids.

TABLE 1

| Entry | Boronic acid |
|---|---|
| BA01 | 3-Aminophenylboronic acid |
| BA02 | 4-chlorophenylboronic acid |
| BA03 | 4-carboxyphenylboronic acid |
| BA04 | Naphthalene-1-boronic acid |
| BA05 | 3-Nitrophenylboronic acid |
| BA06 | Benzene-1,4-diboronic acid |
| BA07 | 2-Naphthylboronic acid |
| BA08 | 1-Thianthrenylboronic acid |
| BA09 | 4-Cyanophenylboronic acid |
| BA10 | 4-Methyl-1-naphthaleneboronic acid |
| BA11 | 6-Methoxy-2-naphthaleneboronic acid |
| BA12 | 6-Ethoxy-2-naphthaleneboronic acid |
| BA13 | 3-Biphenylboronic acid |
| BA14 | 8-Quinolinylboronic acid |
| BA15 | Pyrene-1-boronic acid |
| BA16 | 9,9-Dihexylfluorene-2,7-diboronic acid |
| BA17 | Acenaphthene-5-boronic acid |
| BA18 | 10-Bromoanthracene-9-boronic acid |
| BA19 | 4-(Diphenylamino)phenylboronic acid |
| BA20 | 4-(4'-Methoxybenzyloxy)phenylboronic acid |
| BA21 | 4-(4'-(2-Pentyloxy)phenyl)phenylboronic acid |
| BA22 | 2-(tert-Butyldimethylsilyloxy)naphthalene-6-boronic acid |
| BA23 | 9-Anthraceneboronic acid |
| BA24 | 5-Bromopyridine-3-boronic acid |
| BA25 | 9-Phenanthracenylboronic acid |
| BA26 | 4-Bromo-1-naphthaleneboronic acid |
| BA27 | 2-Aminopyrimidine-5-boronic acid |
| BA28 | Indazole-4-boronic acid |
| BA29 | Fluorene-2-boronic acid |
| BA30 | Indazole-6-boronic acid |

The fluorescence response of SC/SWNT-boronic acids to glucose at 50 mM concentration was measured. Glucose was added (to a final concentration of 50 mM) to the SC/SWNT-boronic acid solutions measured in FIG. 7. The results are summarized in FIG. 8.

Figure 8:
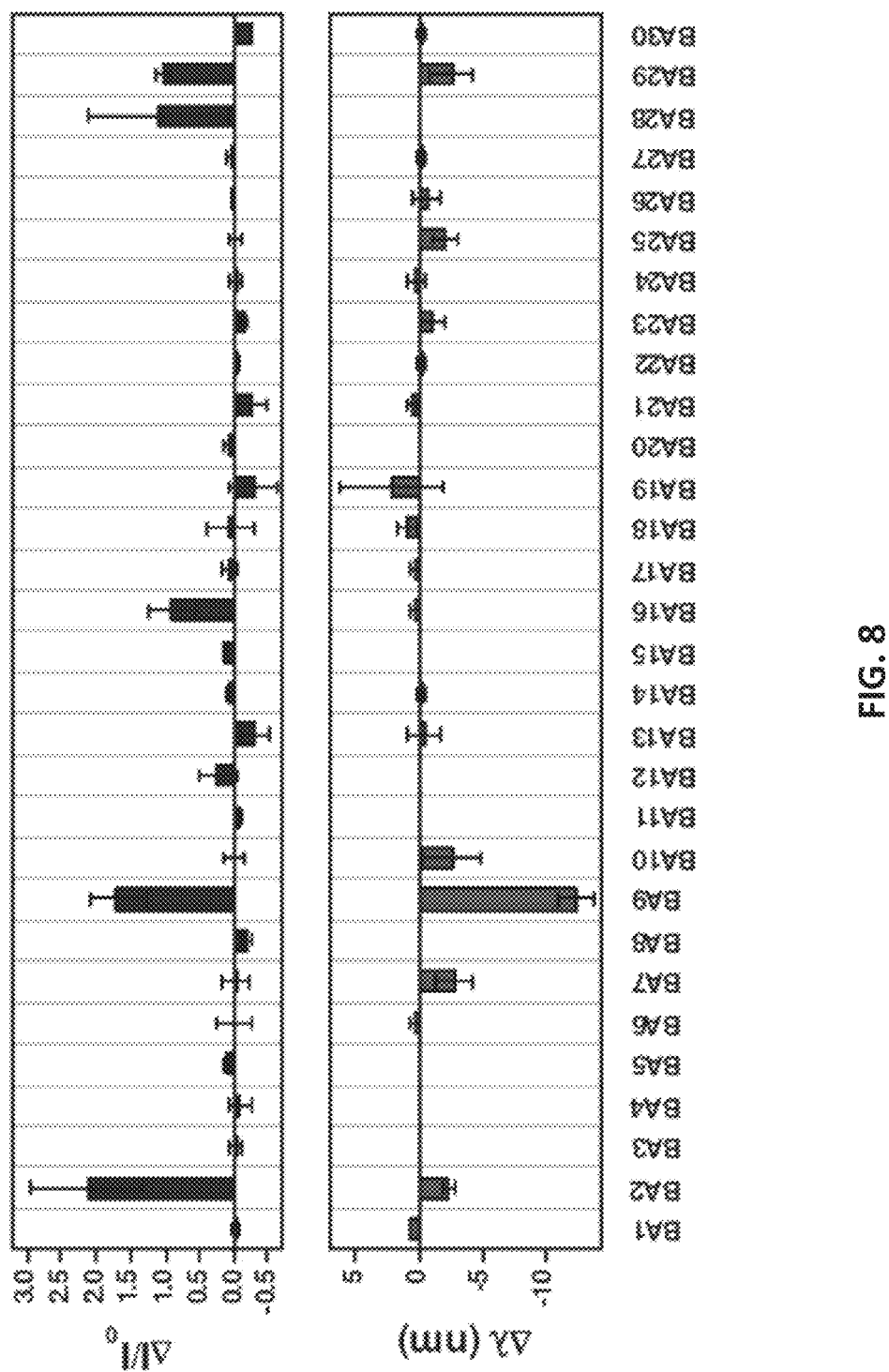
FIG. 8 are graphs summarizing the relative change in fluorescence intensity (top panel) and shift in peak fluorescence wavelength (lower panel) for compositions of sodium cholate-dispersed SWNTs with boronic acids, when exposed to glucose. The error bars are the standard deviation of at least three measurements.
Figure 9:
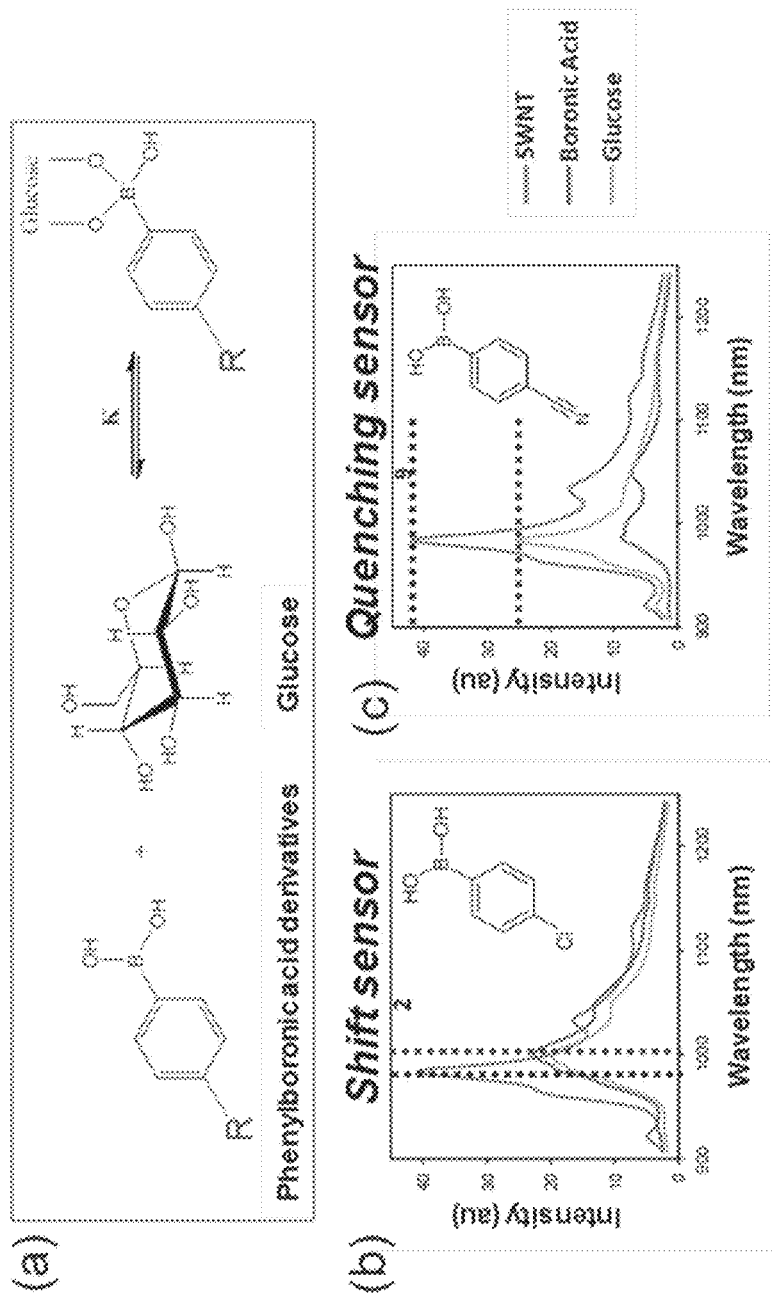
FIG. 9A is a schematic depiction of the reaction between a phenylboronic acid and glucose.
FIG. 9B is a graph illustrating a shift in peak photoluminescence wavelength upon interaction of glucose with a SWNT-surfactant-boronic acid complex.
FIG. 9C is a graph illustrating a change in photoluminescence intensity upon interaction of glucose with a SWNT-surfactant-boronic acid complex. The error bars are the standard deviation of at least three measurements.

FIG. 7 summarizes the fluorescence intensity change and the wavelength shift of (6,5) nanotubes upon addition of 30 different aromatic boronic acids (50 mM) (FIG. 7) and subsequent addition of glucose (50 mM) to the 30 BA-SWNT complexes (FIG. 8). All 30 boronic acids studied here induced some nanotube fluorescence loss, suggesting the adsorption of the boronic acids to the nanotube sidewall through the surfactant layer. This adsorption can be mediated through the anticipated π-π interactions between the sidewall of SWNTs and the aromatic moiety of the boronic acids. Notably, 14 boronic acids also caused a significant red-shift of the emission wavelength upon initial adsorption. The subsequent addition of glucose to the 30 BA-SWNT complex solutions changed the nanotube fluorescence intensity and/or the emission wavelength only for some specific boronic acid structures, which are analyzed in more detail below. The addition of dimethyl sulfoxide (DMSO) to SC/SWNT solutions and the addition of glucose to SC/SWNT solutions without boronic acids did not change the fluorescence spectrum of nanotubes. Moreover, the fluorescence emission of boronic acids was very small in the wavelength range of interest.

Generally, the greatest modulation of SWNT emission occurred for cases where the initial boronic acid adsorption yielded a large fluorescence quenching (>50% of the initial value.) This observation, combined with the fact that glucose invariably increased the resulting emission intensity upon binding, suggested the general mechanism as follows. The boronic acid may adsorb on the nanotube sidewall, through π-π stacking interactions with the pendant aromatic moiety, causing a fluorescence quenching. Glucose binding may disrupt this interaction, partially restoring the decreased emission.

Figure 10:
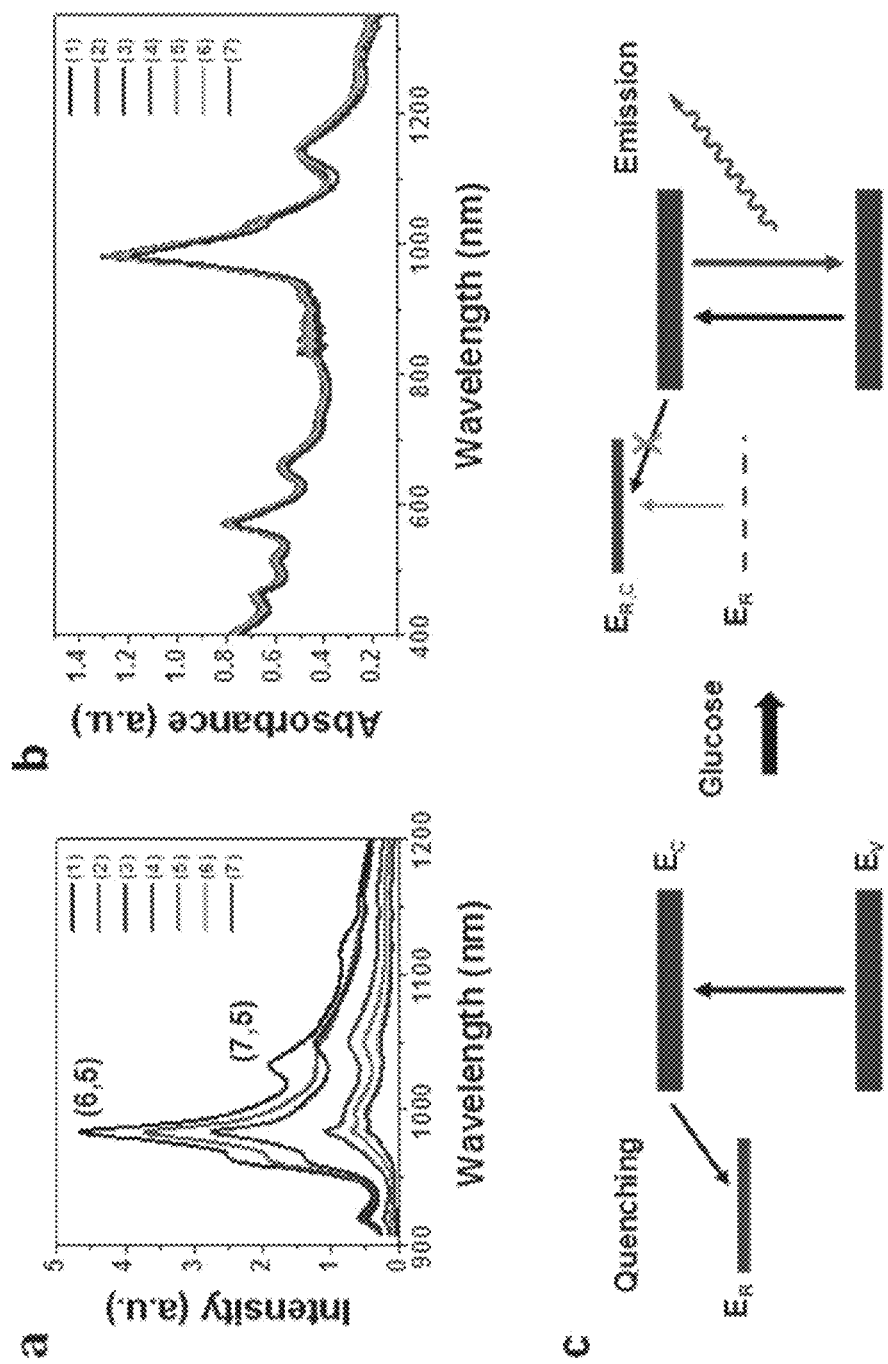
FIG. 10 is a schematic and graphs depicting fluorescence quenching upon introduction of 4-cyanophenylboronic acid (BA9) and fluorescence quenching and recovery mechanisms of the BA-SWNT complex. (a) Fluorescence spectra of nanotubes, showing fluorescence quenching upon stepwise addition of the boronic acid (BA9): (1) starting nanotubes, and after adding the boronic acid of 9.9 mM (2), 19.6 mM (3), 29.1 mM (4), 38.5 mM (5), 47.6 mM (6), and 56.6 mM (7). (b) Absorbance spectra of nanotubes during the quenching process: (1) starting nanotubes, and after adding the boronic acid (BA9) of 5 mM (2), 10 mM (3), 15 mM (4), 25 mM (5), 40 mM (6), and 50 mM (7). (c) Fluorescence quenching mechanism in the absence of glucose (left): a photo-induced excited-electron transfer from the nanotube to the boronic acid. Fluorescence recovery mechanism in the presence of glucose (right): upon the complexation of glucose with the boronic acid, the reduction potential of the complexed boronic acid shifts to a more negative value, which makes the excited-electron transfer from the nanotube to the boronic acid less favorable or impossible, thus leading to fluorescence recovery.

An interesting candidate boronic acid uncovered in this work is 4-cyanophenylboronic acid (BA9) which can cause a relatively rare solvatochromic shift in response to glucose as well as a large intensity change. FIG. 10a shows the fluorescence spectra of the BA-SWNT complex of 4-cyanophenylboronic acid (BA9) upon stepwise addition of the boronic acid to SC/SWNT solutions. The stepwise addition of the boronic acid attenuated the nanotube fluorescence and red-shifted the emission wavelength. A significant red-shift began to clearly appear at the boronic acid concentration of 38.5 mM for (6,5) nanotubes and, interestingly, at a lower boronic acid concentration of 9.9 mM for (7,5) nanotubes (FIG. 10a). The stepwise addition of DMSO to SC/SWNT solutions did not change the fluorescence spectrum.

To assign the mechanism of fluorescence modulation, the absorbance spectrum of the BA-SWNT complex solutions for different concentrations of 4-cyanophenylboronic acid (BA9) was measured (FIG. 10b). Despite the significant fluorescence loss and wavelength shift observed when the boronic acid was added, the absorbance spectra showed no change. A similar behavior was observed with 4-chlorophenylboronic acid (BA2): despite a significant change in the fluorescence spectrum, the BA-SWNT complex of 4-chlorophenylboronic acid (BA2) also showed constant absorbance spectrum. The addition of DMSO to SC/SWNTs and the addition of glucose to SC/SWNTs without boronic acids did not change the absorbance spectrum. The absorbance of the boronic acids themselves was very small in the wavelength range of our interest.

The mechanism of fluorescence intensity loss as a photoinduced excited-state electron transfer from the SWNT conduction band to the boronic acids was non-radiative (i.e. quenching), rather than from a decrease in transition strength (transition bleaching) (as schematically described in FIG. 10c). Previous studies reported that fluorescence bleaching, through a mechanism of a ground-state electron transfer from the nanotube to the oxidizing agent, accompanied a similar loss in the absorbance spectrum. The fluorescence quenching mechanism in this study was also supported by the observation that the red-shift of the emission wavelength of (7,5) nanotube began to appear at a lower boronic acid concentration than that of the (6,5) nanotube. The fluorescence quenching through the excited-state electron transfer mechanism was energetically favorable for large diameter nanotubes with a smaller band gap, because of a larger potential difference between the nanotube conduction band and the boronic reduction potential; the Fermi level of SWNTs became more negative with the increase of SWNT diameters (i.e., with the decrease of SWNT band gaps). Additionally, the constant absorbance indicated that the fluorescence quenching and red-shift process did not involve the aggregation of SWNTs. This may be attributed to the variation in the quenching of nanotubes for different boronic acids to both the different affinity between boronic acids and nanotubes and the different reduction potential of boronic acids relative to the potential of nanotubes.

The reversible fluorescence quenching of the BA-SWNT complex in response to saccharides can provide a new strategy for SWNT-based nIR optical sensing, particularly for glucose. To verify the potential use of this "turn-on" sensing scheme, in which the binding of saccharides to the boronic acid receptor of the BA-SWNT complex increases the nanotube fluorescence, the fluorescence recovery upon addition of glucose was quantified. Because the complexation reversible and reagentless, the binding of saccharides to the aromatic boronic acids was expected to be a function of saccharide concentration. To maximize the sensitivity of the BA-SWNT complex, an optimal level of the boronic acid that maximizes the coverage on the nanotube surface (and thus maximizes the fluorescence quenching), while minimizing free boronic acids that are not conjugated with nanotubes in a solution, was determined. The free boronic acids can also bind with the target analyte, which can interfere with the complexation of the analyte with the receptor boronic acid on the nanotube surface, limiting the sensitivity of the BA-SWNT complex. For 4-cyanophenylboronic acid (BA9), an optimal concentration level of 40 to 50 mM was determined; the fluorescence quenching was saturated at this concentration range (FIG. 10a).

Figure 11:
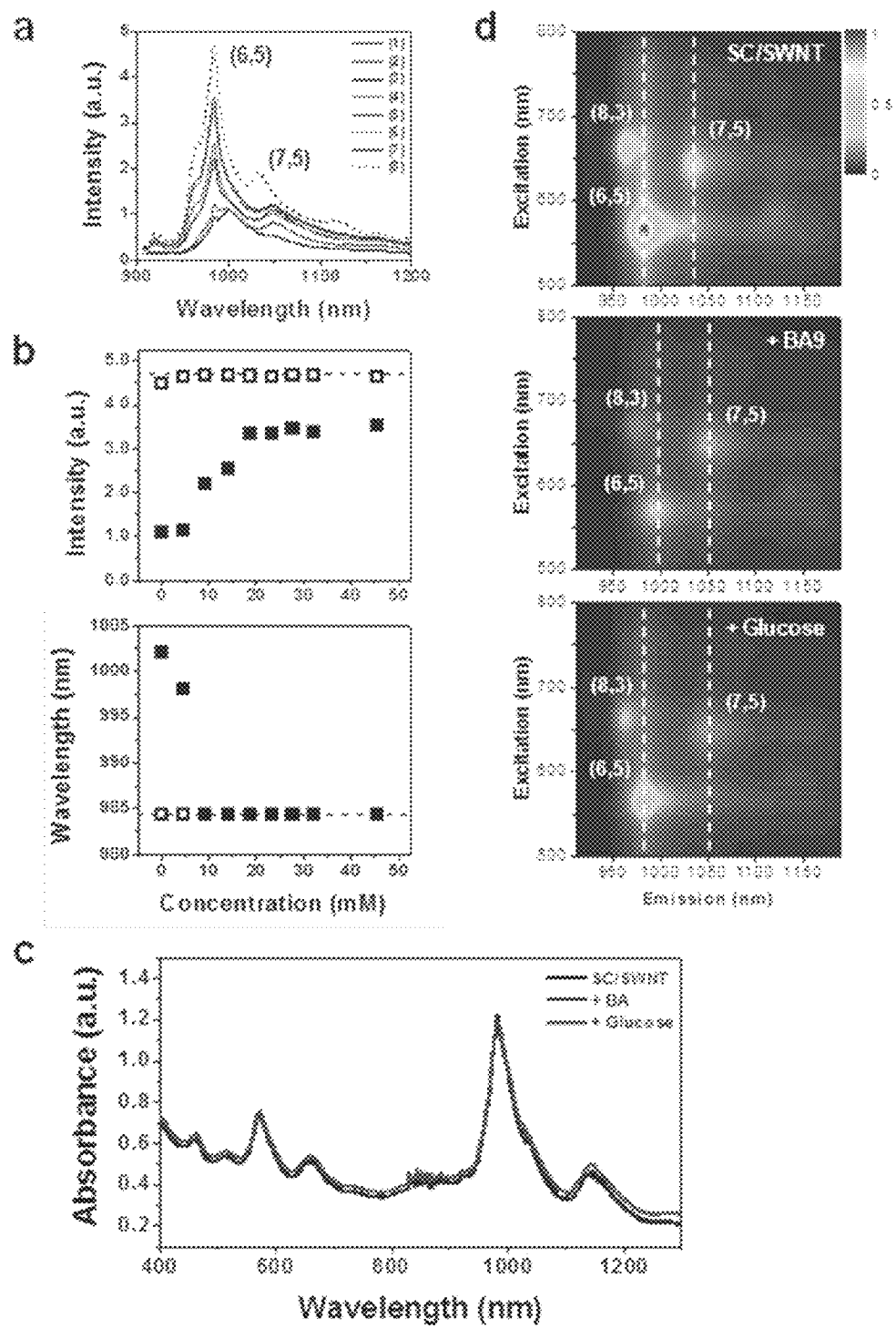
FIG. 11 is a series of graphs depicting fluorescence recovery of the quenched BA-SWNT complex of 4-cyanophenylboronic acid (BA9) in the presence of glucose. (a) Fluorescence spectra upon stepwise addition of glucose: starting BA-SWNT complex prepared with 4-cyanophenylboronic acid (BA9) of 50 mM (1), and after the addition of glucose of 4.7 mM (2), 9.4 mM (3), 14.1 mM (4), 18.7 mM (5), 23.3 mM (6), and 45.5 mM (7). The dashed black line (8) shows the original spectrum of SC/SWNTs. (b) Peak fluorescence intensity (top) and emission wavelength (bottom) of (6,5) nanotubes of the BA-SWNT complex (shown in FIG. 11a) as a function of glucose concentration (solid). The black open square shows the fluorescence intensity (top) and wavelength (bottom) of (6,5) nanotubes of SC/SWNTs without boronic acids as a function of glucose concentration: glucose was added stepwise to the SC/SWNTs without boronic acids. The dashed black line shows the fluorescence intensity (top) and wavelength (bottom) of (6,5) nanotubes of the original SC/SWNTs. (c) Absorbance spectra of the original SC/SWNTs (middle), and the BA-SWNT complex in the absence (bottom) and in the presence of glucose of 54.1 mM (top). (d) Excitation-profile maps of SC/SWNTs (top), the same nanotube sample after the addition of 50 mM 4-cyanophenylboronic acid (BA9) (middle), and the same nanotube sample after the subsequent addition of 50 mM glucose to the BA-SWNT complex.

FIG. 11a shows the fluorescence spectra of the quenched BA-SWNT complex of 4-cyanophenylboronic acid (BA9) upon stepwise introduction of glucose. As determined above, we prepared the BA-SWNT complex solution with the boronic acid concentration of 50 mM. The BA-SWNT complex gradually recovered the quenched fluorescence and the red-shifted emission wavelength with the increase of glucose concentration (FIG. 11a). FIG. 11b shows the fluorescence intensity (top) and the emission wavelength (bottom) of (6,5) nanotubes as a function of glucose concentration (blue square). The addition of 45.5 mM glucose recovered the nanotube fluorescence to a saturated level, reaching 75% of the original SC/SWNT fluorescence level (dashed black line in FIG. 11b). A similar behavior for the BA-SWNT complex of 4-chlorophenylboronic acid (BA2) was also observed. Remarkably, the BA-SWNT complexes can sense the glucose concentration in a physiologically important range (0 to 30 mM), allowing a potential use of this reversible fluorescence quenching and wavelength shift of the BA-SWNT complex for nIR optical sensors for glucose monitoring. FIG. 11c compares the absorbance spectra of the BA-SWNT complex in the absence and in the presence of glucose, and the absorbance spectrum of the starting SC/SWNT. The absorbance spectrum does not show any change upon the addition of glucose, implying that the fluorescence recovery in the presence of glucose may not involve the aggregation and re-dispersion of nanotubes. FIG. 11d shows the excitation-profile maps of SC/SWNTs (top), the same nanotube sample after adding 50 mM 4-cyanophenylboronic acid (BA9) (middle) and after subsequently adding 50 mM glucose (bottom), which showed the reversible quenching of the nanotube fluorescence and/or the reversible shift of the emission wavelength.

The mechanism of the fluorescence recovery can be attributed to the change in the electronic properties of the aromatic moiety of the boronic acid upon binding of glucose (as illustrated in FIG. 10c). The complexation of saccharides with aromatic boronic acids can switch boronic acids from a trigonal neutral form with an $sp^2$ boron atom (an electron-deficient Lewis acid) to a tetrahedral boronate anionic form with an electron-rich $sp^3$ boron atom (increasing its inductive electron-donating ability) at the pH range of 6 to 9. This complexation can alter the reduction potential of the boronic acid more negatively, which can reduce or reverse the potential difference between the nanotube conduction band and the reduction potential of the boronic acid and can make an excited-electron transfer from the nanotube to the boronic acid energetically less favorable, leading to a recovery of nanotube fluorescence.

This fluorescence recovery mechanism can be further supported by the observation that the emission wavelength of (7,5) nanotubes did not recover back to the original value, even at a glucose concentration that saturated the fluorescence recovery, whereas the emission wavelength of (6,5) and (8,3) nanotubes, which have smaller diameters (larger bandgaps) than (7,5) nanotubes, recovered back to the original wavelength. Since (7,5) nanotubes have a more negative conduction band potential than (6,5) and (8,3) nanotubes, the excited-electron transfer from (7,5) nanotubes to the boronic acid complexed with glucose may be still energetically favorable, while the fluorescence quenching of (6,5) and (8,3) may not. The excitation profile maps for 4-cyanophenylboronic acid (BA9) showed this trend, along with the fluorescence recovery in the presence of glucose (FIG. 5d). The observation that (7,5) nanotubes did not fully recover their emission wavelength can also support that the boronic acids complexed with glucose are likely to remain on the surface of the nanotubes.

Other studies reported a similar reversible quenching of SWNTs, where SWNTs interacting with a redox-active dye molecule with a ligand (biotin) showed fluorescence quenching, through a similar excited-state electron transfer mechanism, and further interaction between the ligand and the target analyte (avidin) recovered the quenched fluorescence. In some cases, a strong binding affinity between the receptor (biotin) and the target analyte (avidin) can overcome the weak interaction between the ligand-dye molecule conjugate and the nanotube and thus disrupt the excited-state charge-transfer pathway, leading to the nanotube fluorescence recovery. This is a plausible mechanism, considering a large size of avidin, which can be much larger than biotin and biotin-dye molecule conjugates, and a strong binding affinity between avidin and biotin. Here, however, considering a similarly small size of boronic acids and glucose and the observation that (7,5) nanotubes did not recover their emission wavelength, whereas (6,5) and (8,3) nanotubes did recover (as discussed above), the reduction potential shift of the complexed boronic acid that makes the excited-electron transfer from the nanotube to the complexed boronic acid energetically less favorable may be more likely responsible for the fluorescence recovery in the presence of glucose, than the physical disruption of the charge-transfer pathway between the nanotube and the boronic acid.

Figure 12:
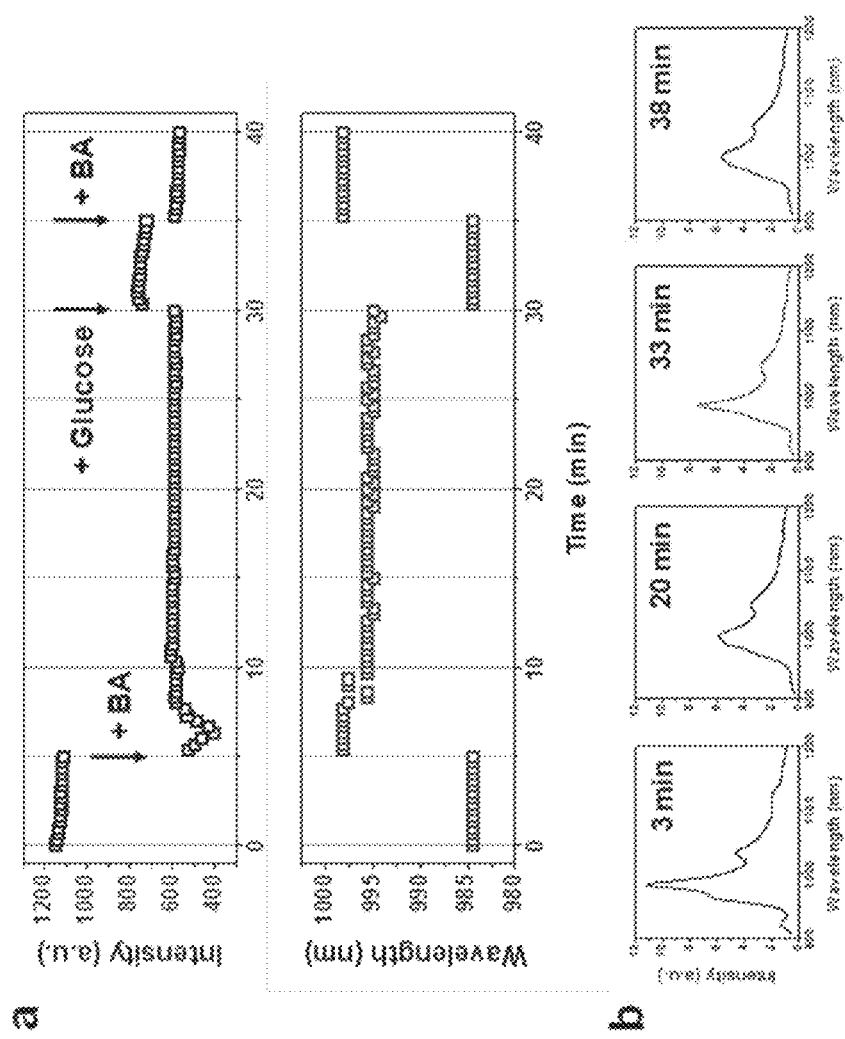
FIG. 12 is a series of graphs depicting dynamic response of nanotube fluorescence upon sequential addition of 4-chlorophenylboronic acid (BA2), glucose, and the boronic acid. (a) Peak fluorescence intensity (top) and wavelength (bottom) of (6,5) nanotubes as a function of time. (b) Corresponding fluorescence spectra at four different times (as indicated in the figures). 4-chlorophenylboronic acid (25 mM) was introduced to the SC/SWNT solutions at 5 min, glucose (50 mM) at 30 min, and 4-chlorophenylboronic acid (25 mM) at 35 min.

The binding and unbinding kinetics were fast enough to potentially enable a dynamic sensing response to glucose. FIG. 12 shows the fluorescence intensity and wavelength of (6,5) nanotubes upon sequential addition of 25 mM 4-chlorophenylboronic acid (BA2) at 5 mM, 50 mM glucose at 30 mM, and 25 mM 4-chlorophenylboronic acid at 35 mM as a function of time (FIG. 12a), along with the corresponding fluorescence spectra at four different times (FIG. 12b). The BA-SWNT complex showed a rapid, reversible dynamic modulation of the nanotube fluorescence upon addition of glucose and the boronic acid, indicating a fast binding and unbinding kinetics of glucose. This rapid, dynamic response of the BA-SWNT complex suggests that the reversible fluorescence quenching mechanism can potentially be used for dynamic sensing of target analytes (e.g., continuous glucose monitoring).

Lastly, design rules can enable sensors of similar composition from the structure of responsive boronic acids. None of the BA-SWNT complexes of the meta-substituted phenylboronic acids (BA1, BA5, BA13, BA20, and BA24) showed substantial responses to glucose: neither the BA-SWNT complexes of the boronic acids with electron-donating groups (amine (BA1), phenyl (BA13), and methoxybenzyloxy (BA20) groups) nor those with electron-withdrawing groups (nitro (BA5) and bromide (BA24) groups) were glucose-responsive. The phenyl derivative (BA13) was the only one in this subset that showed a solvatochromic shift upon initial binding; if the π-stacking arrangement described above was operative, biphenyl boronic acid (BA13) was the only member of the meta-substituted family that would necessarily be oriented in a different configuration. As both aromatic rings attempt to stack, this configuration may be responsible for the shift.

An optimal spatial configuration can be found in the para-substituted phenylboronic acids: BA2, BA3, BA6, BA9, BA19, BA21, and BA27. The two promising candidates recognized in this work come from the electron-withdrawing subset of this family: chloro (BA2) and cyano (BA9) phenylboronic acids; these two species can respond proximately to glucose. The other two electron-withdrawing, para-substituted phenylboronic acids, carboxyphenylboronic acid (BA3) and benzene-diboronic acid (BA6), contain strong hydrophilic moieties in the para-position; this additional hydrophilicity can make it difficult for these species to partition into the hydrophobic surfactant adsorbed phase. The remaining family members (BA19, BA21, and BA27) are electron-donating. Therefore, one conclusion for the sensor design was that para-substituted, electron-withdrawing phenyl boronic acids can modulate SWNT fluorescence in response to glucose, if they are sufficiently hydrophobic as to adsorb on the nanotubes.

The naphthylboronic acids (BA4, BA7, BA10, BA11, BA12, BA14, BA22, and BA26), the anthracene-boronic acids (BA8, BA18, and BA23), and other aromaticboronic acids (BA15, BA16, BA17, BA25, BA28, BA29, BA30) do not show strong responses to glucose, reinforcing the notion that the requisite molecular configuration appears to be para-substitution, electron-withdrawing and strong adsorption to the SWNT surface.

The reactivity of SWNTs with 30 aromatic boronic acids and the fluorescence spectral response of these 30 BA-SWNT complexes to glucose in aqueous solutions was studied. The fluorescence of the BA-SWNT complexes was demonstrated, quenched by the boronic acid receptor via an excited-electron transfer mechanism, and can be selectively recovered upon binding of glucose to the boronic acid receptor on the nanotubes. The BA-SWNT complex in particular modulates its fluorescence intensity with glucose concentrations in a physiologically important range of 5 to 30 mM. This "turn-on" sensing scheme, which uses the reversible fluorescence quenching and wavelength shift of the BA-SWNT complex can provide a new approach for nIR optical sensing of saccharides and glycoproteins. Since various synthetic approaches are available for the design of boronic acids with enhanced specificity and sensitivity, the sensitivity and selectivity of the BA-SWNT complex to saccharides can be further improved or optimized for specific applications, and the further development of the two-component sensing approach that uses SWNTs and boronic acids as read-out units and molecular receptors respectively may also be extended into various biological and chemical sensing applications. One conclusion for sensor design is that para-substituted, electron-withdrawing phenyl boronic acids can modulate the SWNT in response to glucose, if they are sufficiently hydrophobic as to adsorb.

Other embodiments are within the scope of the following claims.

What is claimed is:

1. A composition for sensing an analyte, comprising a complex, wherein the complex includes a photoluminescent nanostructure in an aqueous dispersion and a substituted phenyl boronic acid adsorbed to the photoluminescent nanostructure, wherein the complex has a specific affinity to an analyte and binding of the analyte to the complex changes a fluorescence signal of the photoluminescent nanostructure.

2. The composition of claim 1, wherein the photoluminescent nanostructure is a carbon nanotube.

3. The composition of claim 2, wherein the carbon nanotube is a SWNT.

4. The composition of claim 1, wherein the analyte is a monosaccharide.

5. The composition of claim 4, wherein the monosaccharide is glucose.

6. The composition of claim 5, wherein the boronic acid is selected from the group consisting of: 3-aminophenylboronic acid, 4-chlorophenylboronic acid, 4-carboxyphenylboronic acid, naphthalene-1-boronic acid, 3-nitrophenylboronic acid, benzene-1,4-diboronic acid, 2-naphthylboronic acid, 1-thianthrenylboronic acid, 4-cyanophenylboronic acid, 4-methyl-1-naphthaleneboronic acid, 6-methoxy-2-naphthaleneboronic acid, 6-ethoxy-2-naphthaleneboronic acid, 3-biphenylboronic acid, 8-quinolinylboronic acid, pyrene-1-boronic acid, 9,9-dihexylfluorene-2,7-diboronic acid, acenaphthene-5-boronic acid, 10-bromoanthracene-9-boronic acid, 4-(diphenylamino)phenylboronic acid, 4-(4'-methoxybenzyloxy)phenylboronic acid, 4-(4'-(2-pentyloxy)phenyl)phenylboronic acid, 2-(tert-butyldimethylsilyloxy)naphthalene-6-boronic acid, 9-anthraceneboronic acid, 5-bromopyridine-3-boronic acid, 9-phenanthracenylboronic acid, 4-bromo-1-naphthaleneboronic acid, 2-aminopyrimidine-5-boronic acid, indazole-4-boronic acid, fluorene-2-boronic acid, and indazole-6-boronic acid.

7. The composition of claim 1, wherein the substituted phenyl boronic acid is a para-substituted, electron-withdrawing phenyl boronic acid.

8. A device for sensing an analyte, comprising:
a hydrogel particle encapsulating a composition, wherein the composition includes a complex, wherein the complex includes a photoluminescent nanostructure in an aqueous dispersion and a substituted phenyl boronic acid adsorbed to the photoluminescent nanostructure, wherein the complex has a specific affinity to an analyte and binding of the analyte to the complex changes a fluorescence signal of the photoluminescent nanostructure.

9. The device of claim 8, wherein the photoluminescent nanostructure is a carbon nanotube.

10. The device of claim 9, wherein the carbon nanotube is a SWNT.

11. The device of claim 8, wherein the analyte is a monosaccharide.

12. The device of claim 11, wherein the monosaccharide is glucose.

13. The device of claim 12, wherein the boronic acid is selected from the group consisting of: 3-aminophenylboronic acid, 4-chlorophenylboronic acid, 4-carboxyphenylboronic acid, naphthalene-1-boronic acid, 3-nitrophenylboronic acid, benzene-1,4-diboronic acid, 2-naphthylboronic acid, 1-thianthrenylboronic acid, 4-cyanophenylboronic acid, 4-methyl-1-naphthaleneboronic acid, 6-methoxy-2-naphthaleneboronic acid, 6-ethoxy-2-naphthaleneboronic acid, 3-biphenylboronic acid, 8-quinolinylboronic acid, pyrene-1-boronic acid, 9,9-dihexylfluorene-2,7-diboronic acid, acenaphthene-5-boronic acid, 10-bromoanthracene-9-boronic acid, 4-(diphenylamino)phenylboronic acid, 4-(4'-methoxybenzyloxy)phenylboronic acid, 4-(4'-(2-pentyloxy)phenyl)phenylboronic acid, 2-(tert-butyldimethylsilyloxy)naphthalene-6-boronic acid, 9-anthraceneboronic acid, 5-bromopyridine-3-boronic acid, 9-phenanthracenylboronic acid, 4-bromo-1-naphthaleneboronic acid, 2-aminopyrimidine-5-boronic acid, indazole-4-boronic acid, fluorene-2-boronic acid, and indazole-6-boronic acid.

14. The composition of claim 8, wherein the substituted phenyl boronic acid is a para-substituted, electron-withdrawing phenyl boronic acid.

15. A method for sensing an analyte, comprising:
providing a composition, wherein the composition includes a complex, wherein the complex includes a photoluminescent nanostructure in an aqueous dispersion and a substituted phenyl boronic acid adsorbed to the photoluminescent nanostructure, wherein the complex has a specific affinity to an analyte and binding of the analyte to the complex changes a fluorescence signal of the photoluminescent nanostructure; and
contacting the composition with a sample suspected of containing the analyte.

16. The method of claim 15, wherein the photoluminescent nanostructure is a carbon nanotube.

17. The method of claim 16, wherein the carbon nanotube is a SWNT.

18. The method of claim 15, wherein the analyte is a monosaccharide.

19. The method of claim 18, wherein the monosaccharide is glucose.

20. The method of claim 19, wherein the boronic acid is selected from the group consisting of: 3-aminophenylboronic acid, 4-chlorophenylboronic acid, 4-carboxyphenylboronic acid, naphthalene-1-boronic acid, 3-nitrophenylboronic acid, benzene-1,4-diboronic acid, 2-naphthylboronic acid, 1-thianthrenylboronic acid, 4-cyanophenylboronic acid, 4-methyl-1-naphthaleneboronic acid, 6-methoxy-2-naphthaleneboronic acid, 6-ethoxy-2-naphthaleneboronic acid, 3-biphenylboronic acid, 8-quinolinylboronic acid, pyrene-1-boronic acid, 9,9-dihexylfluorene-2,7-diboronic acid, acenaphthene-5-boronic acid, 10-bromoanthracene-9-boronic acid, 4-(diphenylamino)phenylboronic acid, 4-(4'-methoxybenzyloxy)phenylboronic acid, 4-(4'-(2-pentyloxy)phenyl)phenylboronic acid, 2-(tert-butyldimethylsilyloxy)naphthalene-6-boronic acid, 9-anthraceneboronic acid, 5-bromopyridine-3-boronic acid, 9-phenanthracenylboronic acid, 4-bromo-1-naphthaleneboronic acid, 2-aminopyrimidine-5-boronic acid, indazole-4-boronic acid, fluorene-2-boronic acid, and indazole-6-boronic acid.

21. The composition of claim 15, wherein the substituted phenyl boronic acid is a para-substituted, electron-withdrawing phenyl boronic acid.

* * * * *